(12) United States Patent
Menrad et al.

(10) Patent No.: US 7,851,599 B2
(45) Date of Patent: Dec. 14, 2010

(54) COMBINATION OF AN ANTI-ED—B FIBRONECTIN DOMAIN ANTIBODY—IL-2 FUSION PROTEIN AND GEMCITABINE

(75) Inventors: Andreas Menrad, Ely Cambs (GB); Hans Dietrich Menssen, Berlin (DE); Karola Wagner, Berlin (DE)

(73) Assignee: Philogen S.p.A., Sienna (IT)

( * ) Notice: Subject to any disclaimer, the term of this patent is extended or adjusted under 35 U.S.C. 154(b) by 647 days.

(21) Appl. No.: 11/783,274

(22) Filed: Apr. 4, 2007

(65) Prior Publication Data
US 2009/0110660 A1 Apr. 30, 2009

Related U.S. Application Data

(60) Provisional application No. 60/796,866, filed on May 3, 2006.

(30) Foreign Application Priority Data

Apr. 7, 2006 (EP) .................................. 06090054

(51) Int. Cl.
C07K 19/00 (2006.01)
C07K 14/00 (2006.01)
C12P 21/08 (2006.01)
A61K 38/00 (2006.01)
A61K 31/00 (2006.01)

(52) U.S. Cl. ................. 530/387.3; 530/351; 530/388.1; 514/2; 514/12; 514/49; 514/50; 424/85.2; 424/178.1; 424/179.1; 424/180.1; 424/278.1; 536/28.5; 536/28.51

(58) Field of Classification Search ........................ None
See application file for complete search history.

(56) References Cited

U.S. PATENT DOCUMENTS

2004/0013640 A1 1/2004 Zardi et al.
2007/0189963 A1 8/2007 Neri

FOREIGN PATENT DOCUMENTS

WO    WO 9958570 A    11/1999

OTHER PUBLICATIONS

Rudikoff et al (Proc Natl Acad Sci USA 1982 vol. 79 p. 1979).*
Casset et al. (2003) BBRC 307, 198-205.*
Chen et al. J. Mol. Bio. (1999) 293, 865-881.*
Vajdos et al. (2002) J. Mol. Biol. 320, 415-428.*
Wu et al. J. Mol. Biol. (1999) 294, 151-162.*
Menard A et al, "ED-B fibronectin as a target for antibody-based cancer treatment", Expert Opinion on Therapeutic Targets, Ashley Publications, London, GB, vol. 9 No. 3, Jun. 2005, pp. 491-500.
Wagner Karola et al, "Therapeutic efficacy of the targeted cytokine L19-Il2 in orthotopic animal models of pancreatic cancer", Gastroenterology, vol. 128 No. 4 suppl.2, Apr. 2005, p. A78, &, Annual meeting of the American-Gastroenterological-Association/Digestive-Disease-Week; Chicago, IL, USA; May 14-19, 2005.
Menard A et al, "Therapeutic efficacy of the targeted immunocytokine L19-IL2 in orthotopic animal models for pancreatic-and hepatocellular carinoma", retrieved from http://www.charite.de/fabisch.
Carnemolla Barbara et al, "Enhancement of the antitumor properties of interleukin-2 by its targeted delivery to the tumor blood vessel extracellular matrix", Blood, W.B. Saunders Company, Orlando, FL, US, vol. 99 No. 5, Mar. 1, 2002, pp. 1659-1665.
Kaspar Manuela et al, "Fibronectin as target for tumor therapy", International Journal of Cancer. Journal International Du Cancer, Mar. 15, 2006, pp. 1331-1339.
Schwarz R E et al, "An orthotopic in vivo model of human pancreatic cancer", Surgery, Sep. 1999, pp. 562-567.
Toschi L et al, "Role of gemcitabine in cancer therapy", Future Oncology, London, England, Feb. 2005, vol. 1 No. 1 Feb. 2005, pp. 7-17.
Gramont De A et al, "Investigating the Potential of Bevacizumab in Other Indications: Metastatic Renal Cell, Non-Small Cell Lung, pancreatic and breast cancer", Oncology, S. Karger AG, Basel, CH, vol. 69 No. suppl 3, Nov. 2005, pp. 46-56.
Halin C et al, "Antibody-based targeting of Angiogenesis", Critical Reviews in Therapeutic Drug Carrier Systems, vol. 18 No. 3, 2001, pp. 299-339.
J. Yang et al., "Randomized Study of High-Dose and Low-Dose Interleukin-2 in Patients With Metastatic Renal Cancer", Journal of Clinical Oncology, vol. 21, No. 16 (Aug. 16, 2003) pp. 3127-3132.
U. Keilholz et al., "Dacarbazine, Cisplatin, and Interferon-Alfa-2b With or Without Interleukin-2 in Metastatic Melanoma : A Randomized Phase III Trial (18951) of the European Organisation for Research and Treatment of Cancer Melanoma Group", Journal of Clinical Oncology, vol. 23, No. 27 (Sep. 20, 2005) pp. 6747-6755.
D. Moosmayer et al., "Bispecific Antibody Pretargeting of Tumor Neovasculature for Improved Systemic Radiotherapy of Solid Tumors", Clin. Cancer Res., vol. 12, No. 18 (Sep. 15, 2006) pp. 5587-5595.
J. Yang et al., "An Ongoing Prospective Randomized Comparison of Interleukin-2 Regimens for the Treatment of Metastatic Renal Cell Cancer", Cancer J. Sci. Am., vol. 3 (1997) pp. S79-S84.
A. Hauschild et al., "Dacarbazine and Interferon α With or Without Interleukin 2 in Metastatic Melanoma : A Randomized Phase III Multicentre Trial of the Dermatologic Cooperative Oncology Group (DeCOG)", British Journal of Cancer, vol. 84, No. 8 (2001) pp. 1036-1042.
M. Atkins et al., "High-Dose Recombinant Interleukin 2 Therapy for Patients With Metastatic Melanoma: Analysis of 270 Patients Treated Between 1985 and 1993", Journal of Clinical Oncology, vol. 17, No. 7 Jul. 1999 pp. 2105-2116.

(Continued)

*Primary Examiner*—Gary B. Nickol
*Assistant Examiner*—Daniel C Gamett
(74) *Attorney, Agent, or Firm*—Millen, White, Zelano, Branigan, P.C.

(57) ABSTRACT

The invention refers to the use of L19IL2 for treatment of pancreatic cancer. In another embodiment, the invention relates to a combination (i) of a fusion protein, comprising an Interleukin 2 part and an antibody part, specifically recognizing the extra domain B of fibronectin (ED-B-fibronectin), and (ii) gemcitabine.

20 Claims, 8 Drawing Sheets

OTHER PUBLICATIONS

Figure 1:
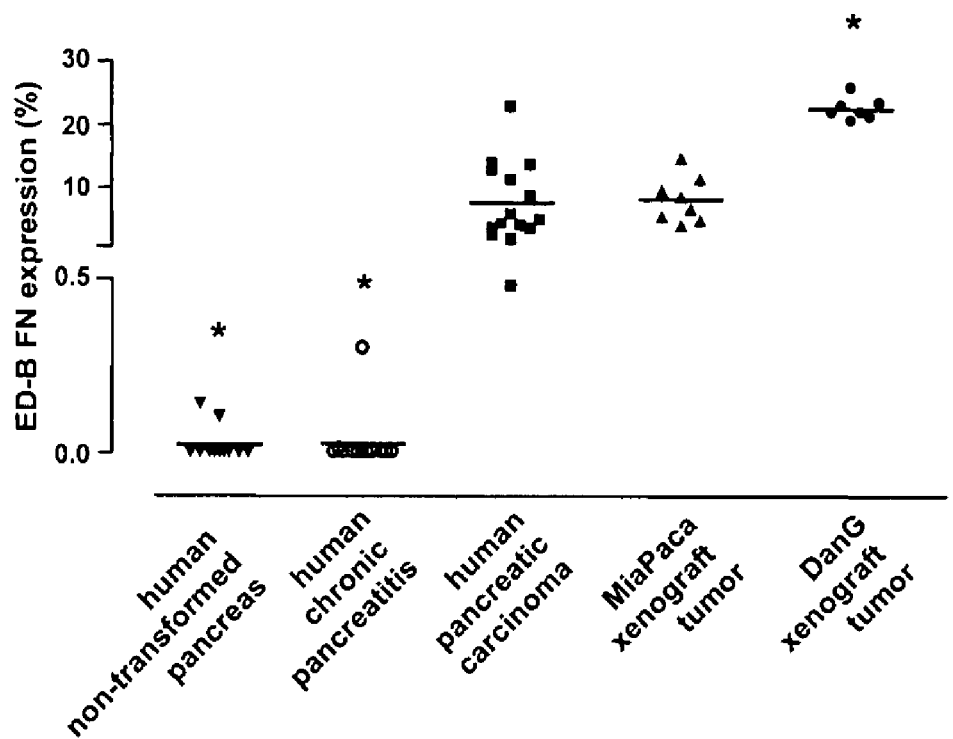

J. Plate et al., "Effect of Gemcitabine on Immune Cells in Subjects with Adenocarcinoma of the Pancreas", Cancer Immunol. Immunother., vol. 54 (2005) pp. 915-925.

A. Nowak et al., "Gemcitabine Exerts a Selective Effect on the Humoral Immune Response : Implications for Combination Chemo-Immunotherapy", Cancer Research, vol. 62 Apr. 15, 2002 pp. 2353-2358.

A. Nowak et al., "Synergy between Chemotherapy and Immunotherapy in the Treatment of Established Murine Solid Tumors", Cancer Research, vol. 63 (Aug. 1, 2003) pp. 4490-4496.

Nowak et al. "Gemcitabine Exerts a Selective Effect on the Humoral Immune Response: Implications for Combination Chemo-immunotherapy." *Cancer Research*, 62, 2353-2358, Apr. 15, 2002.

Gramont et al. "Investigating the Potential of Bevacizumab in Other Indications: Metastatic Renal Cell, Non-Small Cell Lung, Pancreatic and Breast Cancer." *Oncology* 69 (suppl 3):46-56, 2005.

Toschi et al, "Role of gemcitabine in cancer therapy." *Future Oncology*, vol. 1, No. 1, pp. 7-17, 2005.

Daikeler et al. "The influence of gemcitabine on the CD4/CD8 ratio in patients with solid tumours." *Oncology Reports*, 4: 561-564, 1997.

Bonnema et al. "Cytokine-enhanced NK cell-mediated cytotoxicity. Positive modulatory effects of IL-2 and IL-12 on stimulus-dependent granule exocytosis." *The Journal of Immunology*, vol. 152, Issue 5 2098-2104, 1994.

Wang et al. "IL-2 induces STAT4 activation in primary NK cells and NK cell lines, but not in T cells." *The Journal of Immunology*, vol. 1; 162(1):299-304, 1999.

* cited by examiner

Fig2
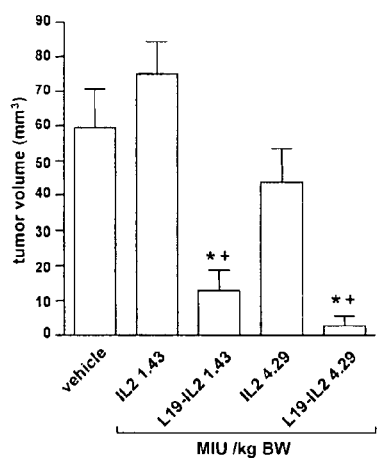
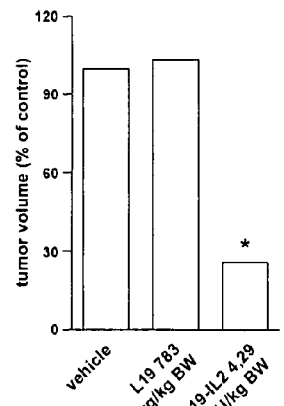
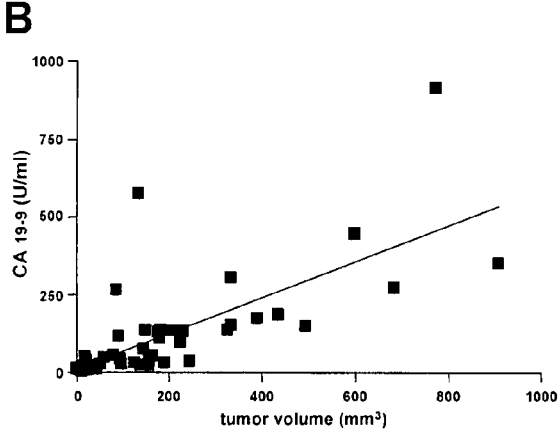
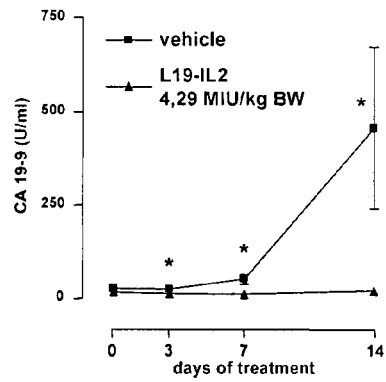
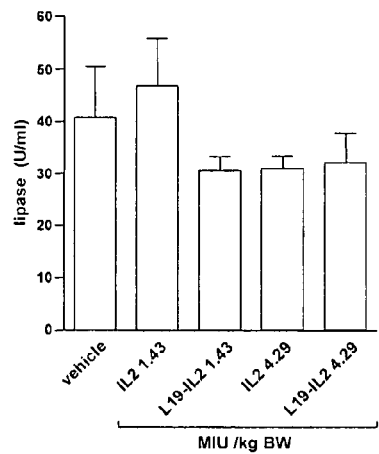
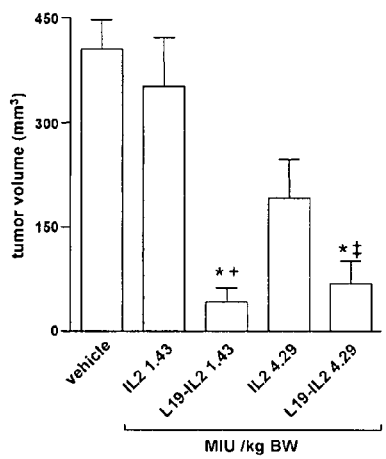

Fig4
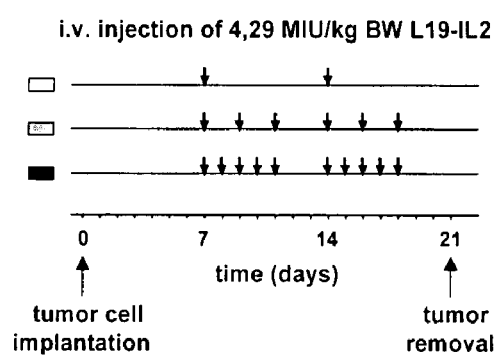
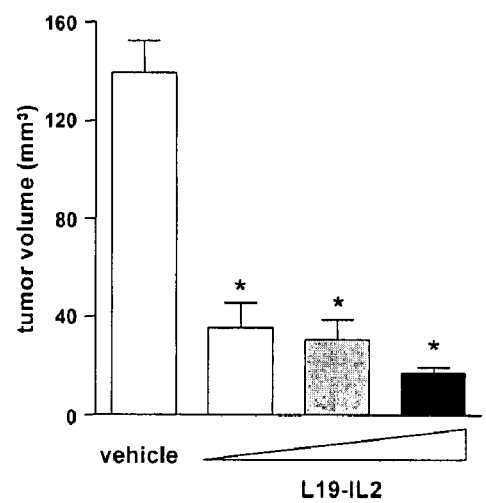

Fig7
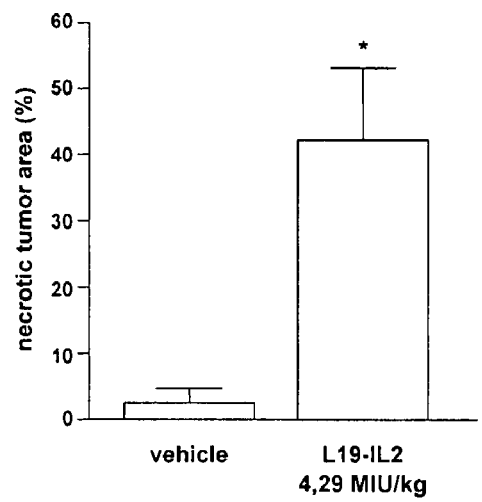
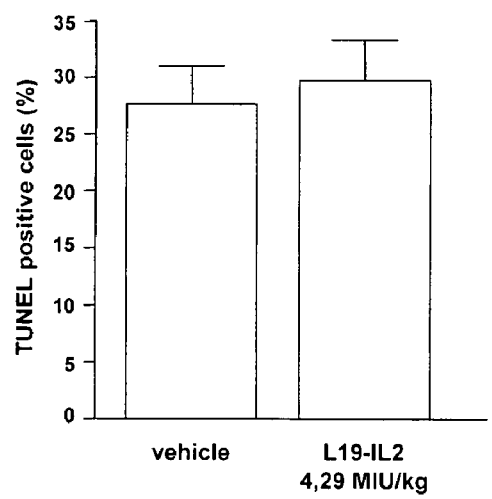
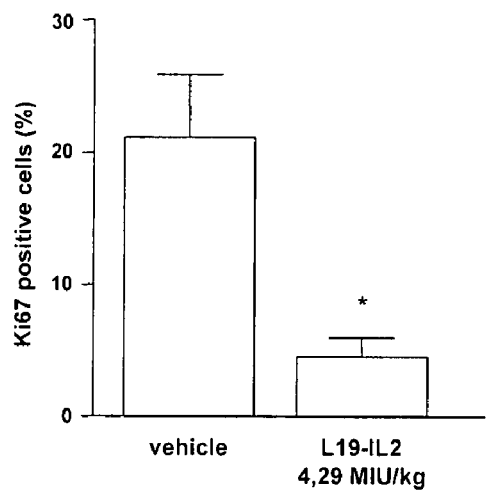

Fig8
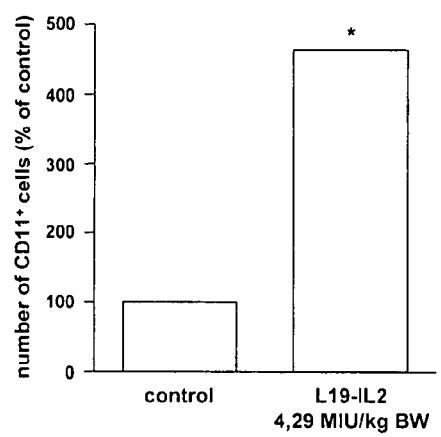
A
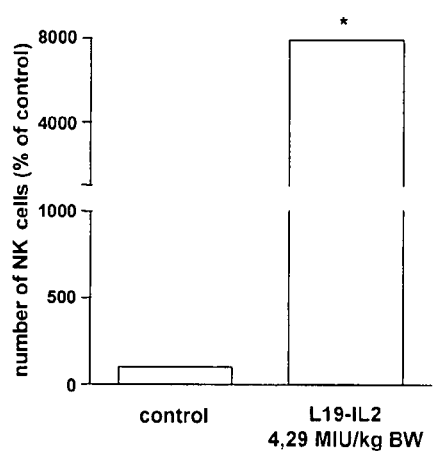
B
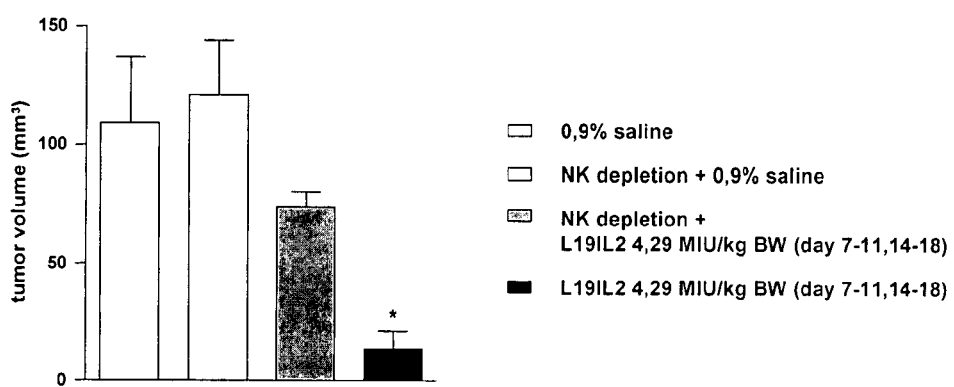
C

COMBINATION OF AN ANTI-ED—B FIBRONECTIN DOMAIN ANTIBODY—IL-2 FUSION PROTEIN AND GEMCITABINE

This application claims the benefit of U.S. Ser. No. 60/796,866, filed May 3, 2006, which is incorporated by reference herein.

The invention relates to a combination of (i) a fusion protein, comprising an Interleukin 2 part and an antibody part, specifically recognising the extra domain B of fibronectin (ED-B-fibronectin), and (ii) Gemcitabine, and its use for treatment of cancer, in particular pancreatic cancer.

STATE OF THE ART

Adenocarcinoma of the pancreas represents the fifth leading cause of cancer related death in industrialized Western Countries. (Parker S L, Tong T, Bolden S, Wingo P A. Cancer statistics, 1997. CA Cancer J Clin 1997;47:5-27). The prognosis of patients diagnosed with pancreatic cancer is extremely poor with an estimated overall 5-year survival rate of only 1-4%. Surgical resection provides the only potentially curative treatment, but locally extended or metastasized disease precludes surgical treatment in most cases. (Rosewicz S, Wiedenmarm B. Pancreatic carcinoma. Lancet 1997;349:485-489; Cohen S J, Pinover W H, Watson J C, Meropol N J. Pancreatic cancer. Curr Treat Options Oncol 2000;1:375-386). Moreover currently available palliative strategies have little impact on the aggressive course of this neoplasm, achieving objective response rates of less than 20% with a dismal median survival of 4-6 months. (Burris H A, III, Moore M J, Andersen J, Green M R, Rothenberg M L, Modiano M R, Cripps M C, Portenoy R K, Storniolo A M, Tarassoff P, Nelson R, Dorr F A, Stephens C D, Von Hoff D D. Improvements in survival and clinical benefit with gemcitabine as first-line therapy for patients with advanced pancreas cancer: a randomized trial. J Clin Oncol 1997;15:2403-2413). Current chemotherapeutic agents and radiation treatments rely on the rapidly dividing nature of tumor cells, thereby suffering from poor selectivity. Unacceptable toxicities towards proliferating nonmalignant cells limit dose escalation and prevent the administration of a curative dose. Moreover most chemotherapeutic agents do not preferentially accumulate at the tumor site (Bosslet K, Straub R, Blumrich M, Czech J, Gerken M, Sperker B, Kroemer H K, Gesson J P, Koch M, Monneret C. Elucidation of the mechanism enabling tumor selective prodrug monotherapy. Cancer Res 1998;58: 1195-1201). Due to high interstitial pressure and irregular tumor vasculature, chemotherapeutic agents fail to achieve adequate levels within the tumor (Folli S, Pelegrin A, Chalandon Y, Yao X, Buchegger F, Lienard D, Lejeune F, Mach J P. Tumor-necrosis factor can enhance radio-antibody uptake in human colon carcinoma xenografts by increasing vascular permeability. Int J Cancer 1993;53:829-836; Jain R K. Transport of molecules in the tumor interstitium: a review. Cancer Res 1987;47:3039-3051). However, the clinical development of systemic TNFα failed, since the doses that would be necessary for an anti-cancer efficacy were associated with unacceptable toxicity. (Jones A L, Selby P. Tumor necrosis factor: clinical relevance. Cancer surveys 1989;8:817-836. One promising avenue to circumvent these obstacles consists in the targeted delivery of therapeutic agents to the tumor microenvironment via antigen specific ligands e.g. antibodies specific for tumor-associated markers. In particular, targeting of markers associated with tumor angiogenesis represents an appealing therapeutic strategy for a number of reasons. First, targets which are selectively expressed around tumor neo-vasculature and in the tumor stroma are easily accessible to intravenously administered antibody derivatives. Second, markers of neo-vasculature are typically produced by endothelial cells and/or fibroblasts, which are genetically more stable than tumor cells. Third, as angiogenesis is a prerequisite of tumor growth and metastasis, the selective delivery of toxic agents to new-forming blood vessels should offer a therapeutic benefit. Finally, as angiogenesis, i.e. the growth of new capillaries from preexisting blood vessels, is characteristic of all aggressive solid tumors, these targets can be regarded as pan-tumoral antigens (Halin C, Zardi L, Neri D. Antibody-based targeting of angiogenesis. News Physiol Sci 2001;16:191-194; Alessi P, Ebbinghaus C, Neri D. Molecular targeting of angiogenesis. Biochim Biophys Acta 2004;1654: 39-49).

One of the most selective oncofetal markers associated with neo-angiogenesis and tissue remodeling known so far represents the extra domain B (ED-B) of Fibronectin (FN) (Castellani P, Viale G, Dorcaratto A, Nicolo G, Kaczmarek J, Querze G, Zardi L. The fibronectin isoform containing the ED-B oncofetal domain: a marker of angiogenesis Int J. Cancer. 1994 Dec. 1;59(5):612-8. Erratum in: Int J Cancer 1995 Jul. 4;62(1):118. FNs are high molecular-weight extracellular matrix (ECM) components abundantly expressed in a range of healthy tissues and body fluids. Various different FN isoforms can be generated due to alternative splicing at the level of the primary transcript. The ED-B, a small domain of 91 amino acids, which is identical in sequence in mouse and man, is usually absent in both plasma and tissue-fibronectin, except for some blood vessels of the regenerating endometrium and the ovaries. (Alessi P, Ebbinghaus C, Neri D. Molecular targeting of angiogenesis. Biochim Biophys Acta 2004;1654:39-49; Viti F, Tarli L, Giovannoni L, Zardi L, Neri D. Increased binding affinity and valence of recombinant antibody fragments lead to improved targeting of tumoral angiogenesis. Cancer Res 1999;59:347-352). However, it may become inserted in the fibronectin molecule during active tissue remodeling associated with neo-angiogenesis, thereby accumulating around the neo-vasculature and in the stroma of malignant tumors and in other tissues undergoing remodeling and angiogenesis. Recently, a number of good quality antibodies specific for the ED-B domain of fibronectin have been generated. In particular, the human single chain Fv antibody fragment scFv(L19), which displays a picomolar binding affinity for ED-B, has been verified to selectively target tumor neovasculature, both in experimental tumor models (Viti F, Tarli L, Giovannoni L, Zardi L, Neri D. Increased binding affinity and valence of recombinant antibody fragments lead to improved targeting of tumoral angiogenesis. Cancer Res 1999;59:347-352) and in patients with cancer (Santimaria M, Moscatelli G, Viale G L, Giovannoni L, Neri G, Viti F, Leprini A, Borsi L, Castellani P, Zardi L, Neri D, Riva P. Immunoscintigraphic detection of the ED-B domain of fibronectin, a marker of angiogenesis, in patients with cancer. Clin Cancer Res 2003;9:571-579), thus paving the way for the selective delivery of therapeutic agents to tumor neovasculature. In this context, Interleukin 2 (IL-2) has been characterized as one of the most potent anti-tumor cytokines. It exhibits a panoply of immune regulatory effects, including the stimulation of various anti-tumor effector cells (Rosenberg S A. Progress in the development of immunotherapy for the treatment of patients with cancer. J Intern Med 2001;250:462-475). However, despite being approved for the clinical treatment of metastatic renal cell carcinoma, systemically applied IL-2 has not been proven as successful as one had hoped. Therapeutic efficacy of systemically applied IL-2 is thwarted by its serious, potentially life-threatening side effects (e.g. orthostatic hypotension, vascular leak syndrome and profound malaise) that limit dose escalation and pre-vent the administration of a curative dose (Bubenik J, Den Otter W, Huland E. Local cytokine therapy of cancer: interleukin-2, interferons and related cytokines. Cancer Immunol Immunother 2000;49:116-122; Baluna R, Rizo J, Gordon B E, Ghetie V, Vitetta E S. Evidence for a structural motif in toxins and interleukin-2 that may be responsible for binding to endothelial cells and initiating vascular leak syndrome. Proc Natl Acad Sci U S A 1999;96:3957-3962). Additionally, the rapid degradation or elimination of IL-2 delivered systemically further decreases its effectiveness. On the other hand, local administration of IL-2 has been more successful and has resulted in the control of malignant effusions and the generation of significant remission of established lesions (Bubenik J, Den Otter W, Huland E. Local cytokine therapy of cancer: interleukin-2, interferons and related cytokines. Cancer Immunol Immunother 2000;49:116-122; Den Otter W, Dobrowolski Z, Bugajski A, Papla B, Van Der Meijden A P, Koten J W, Boon T A, Siedlar M, Zembala M. Intravesical interleukin-2 in T1 papillary bladder carcinoma: regression of marker lesion in 8 of 10 patients. J Urol 1998;159:1183-1186; Baselmans A H, Koten J W, Battermann J J, Van Dijk J E, Den Otter W. The mechanism of regression of solid SL2 lymphosarcoma after local IL-2 therapy. Cancer Immunol Immunother 2002;51:492-498; Krastev Z, Koltchakov V, Popov D, Alexiev A, Koten J W, Den Otter W. A case of hepatocellular carcinoma (HCC): treatment with local application of alcohol and interleukin 2 (IL-2). Hepatogastroenterology 2003;50:1647-1649). In this regard the targeted upload of the cytokine IL-2 to tumor microenvironment by conjugating it to the scFv L19, specific for the ED-B of FN, appears to be an attractive concept to enhance the therapeutic index of IL-2 and at the same time diminish its toxic side effects. Previously, it has been verified that L1 g-mediated delivery of IL-2 to tumor microenvironment enhances the therapeutic performance of this cytokine using subcutaneous mouse models of teratocarcinoma, small-cell lung cancer, and colon adenocarcinoma (Carnemolla B, Borsi L, Balza E, Castellani P, Meazza R, Berndt A, Ferrini S, Kosmehl H, Neri D, Zardi L. Enhancement of the antitumor properties of interleukin-2 by its targeted delivery to the tumor blood vessel extracellular matrix. Blood 2002;99:1659-1665).

Tumours cannot grow beyond a certain mass without the formation of new blood vessels (angiogenesis), and a correlation between micro-vessel density and tumour invasiveness has been reported for a number of tumours (Folkmann (1995) Nat. Med., Vol. 1, p. 27). Molecules capable of selectively targeting markers of angiogenesis create clinical opportunities for the diagnosis and therapy of tumours and other diseases characterised by vascular proliferation, such as rheumatoid arthritis, diabetic retinopathy and age-related macular degeneration (O'Reilly et al. (1996) Nat. Med. Vol.: 2 p. 689 et seqq; O'Reilly et al. (1997) Cell, Vol.: 88, p. 277 et seqq; Friedlander et al. (1995) Science Vol.: 270, p. 1500 et seqq; Pasqualini et al. (1997) Nat. Biotechnol. Vol.: 15 p. 542 et seqq; Huang et al. (1997) Science, Vol.: 275, p. 547 et seqq; Kim et al. (1993) Nature, Vol.: 362, p. 841 et seqq; Schmidt-Erfurth et al. (1997) Br. J. Cancer, Vol.: 75, p. 54 et seqq).

EP 0 122 707 discloses nucleosides containing difluorcarbohydrate groups for treatment of viruses. EP 0 184 365 describes the use of gemcitabine (1-(4-Amino-2-oxo-1H-pyrimidin-1-yl)-2-desoxy-2,2-difluororibose or 2'-deoxy-2',2'-difluorocytidine) as a medicament for the treatment of susceptible neoplasms. The synthesis of gemcitabine is described e.g. in EP 0 184 365 and EP 727 433. The term "Gemcitabine" is to be understood as 2'-deoxy-2',2'-difluorocytidine as well as physiologically acceptable salts thereof, in particular the hydrochloride salt thereof. The hydrochloride salt of 2'-deoxy-2',2'-difluorocytidine is commercially available under the trade name Gemzar.

Pancreatic cancer is a chemoresistant cancer, and standalone radiation therapy of pancreatic cancer does not result in a survival benefit for the patient. Several clinical trials describe the combination of radiation therapy plus gemcitabine (Blackstock A. W. et al. J. Clin. Oncol. 17:2208-2212, 1999; Mose S. et al. Strahlenther Onkol. Vol.: 178, pages 59-70, 2002). The use of gemcitabine as radiosensitizer in combination with radioimmunotherapy with antibodies for the treatment of pancreatic cancer was investigated in several animal models. Gold D V et al. (Clin. Can. Res., Vol.: 9, 3929s-3937s, 2003) describe the use of Y-90- and I-131-labelled monoclonal anti-bodies directed against MUC1 mucin in combination with Gemcitabine. The combined treatment resulted in significantly improved treatment efficacies.

Interleukin-2 (IL-2), a four alpha helix bundle cytokine produced by T helper 1 cells, plays an essential role in the activation phases of both specific and natural immune responses (Taniguchi et al. (1993) Cell, Vol.: 73, pages 5-8). IL-2 promotes proliferation and differentiation of activated T and B lymphocytes and of natural killer (NK) cells, and induces cytotoxic T cell (CTL) activity and NK/lymphokine activated killer (LAK) anti-tumour cytotoxicity. IL-2 has been used in immunotherapy approaches of several human tumours (Rosenberg (1992) J. Clin. Oncol. Vol.: 10, pages 180-199). Administration of recombinant IL-2 (rIL-2) alone or in combination with adoptively transferred lymphoid cells has resulted in the regression of established tumours in both animal models and patients. However, its in vivo therapeutic efficacy is limited by its rapid clearance and, at high doses, by a severe toxicity mainly related to a vascular leak syndrome (Siegel and Puri (1991) Interleukin-2 toxicity in J. Clin. Oncol. Vol.: 9 pages 694-704). Delivery of IL-2 to the tumour site by means of an antibody directed against a cell-surface tumour marker may allow achievement of active local concentrations of IL-2, as well as reducing toxicities associated to systemic administration (Lode et al. (1998) Pharmacol. Ther. Vol.: 80, pages 277-292).

The presence of IL-2 bound at a tumour cell surface results in activation and/or targeting of effector cells of the immune system, either $CD8^+$ cytotoxic T cells or natural killer (NK) cells, and in the induction of an efficient anti-tumour immune response. T- or NK-cells receive one signal through receptor(s) (for instance T-cell receptor for T cells) specifically recognising appropriate ligands at the tumour cell surface, and a second signal through IL-2 receptor chains by IL-2, also localised at the tumour cell surface (Lode et al., 1999, PNAS USA, 96: 8591-8596 and references therein).

The ED-B domain of fibronectin, a sequence of 91 amino acids identical in mice, rats and humans, which is inserted by alternative splicing into the fibronectin molecule, specifically accumulates around neovascular structures and represents a target for molecular intervention (Zardi et al. (1987) EMBO J. Vol.: 6, pages 2337-2342; Carnemolla et al. (1989) J. Cell Biol. Vol: 108, pages 1139-1148, further Castellani et al, (1994) Int. J. Cancer, Vol. 59, pages 612-618). Using the human recombinant antibody L19 directed to the ED-B domain, the possibility of in vivo neovasculature targeting has been demonstrated in different tumour models (Tarli et al. (1999) Blood, Vol.: 94, pages 192-198; Viti et al. (1999) Cancer Res. Vol.: 347).

Monoclonal antibodies specifically recognising the ED-B-fibronectin domain are described in WO 97/45544.

Monoclonal antibody L19 is described in WO 99/58570.

The fusion protein L19IL2 is described for example in the WO 01/62298. WO 01/62298 on page 8, line 12 refers to the L19VH and L19VL domain sequences described in Pini et al. (1998) J. Biol. Chem. 273: 21769-21776. Pini et al. describes parts of the sequence of L19 in Table II on page 21772. L19 has the EMBL accession Number AJ 006113.

There is a strong medical need for a medicament to effectively treat pancreatic cancer. The present invention makes available novel and effective medicaments, which are suitable for the treatment of pancreatic cancers.

In one embodiment, the present invention relates to the use of at least one fusion protein for manufacture of a medicament for treatment of pancreatic cancer,
wherein the fusion protein comprises
an antibody-part,
specifically recognising the ED-B-fibronectin domain and
an Interleukin-2 part.

Another embodiment of the present invention relates to a combination comprising at least a fusion protein and gemcitabine,
wherein the fusion protein comprises
an antibody-part,
specifically recognising the ED-B-fibronectin domain and
an Interleukin-2 part.

The term "Gemcitabine" is to be understood as 2'-deoxy-2',2'-difluorocytidine as well as physiologically acceptable salts thereof, in particular the hydrochloride salt thereof. The hydrochloride salt of 2'-deoxy-2',2'-difluorocytidine is commercially available under the trade name Gemzar.

Gemcitabine in its base form has the formula

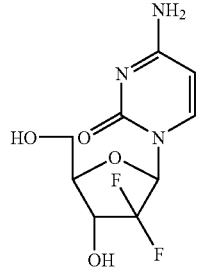

We observed selective overexpression of ED-B FN in human pancreatic carcinoma as determined by immunohistochemistry, whereas no ED-B FN was detectable in human non-transformed pancreas and chronic pancreatitis tissue. In analogy to the human situation, a qualitatively and quantitatively comparable ED-B FN expression pattern was confirmed in primary pancreatic tumors as well as in lymph node and liver metastases of the orthotopic mouse models investigated in this study.

Using these mouse models as clinically representative in vivo models, we surprisingly demonstrated that administration of L19IL2 efficiently inhibited the growth of established primary pancreatic tumors and reduced or eliminated lymph node metastases, while untargeted IL-2 elicited minor or no therapeutic effects. Also, the anti-tumor activity of L19IL2 was exclusively mediated by IL-2, as shown by application of the scFv L19 antibody fragment alone, which failed to achieve any therapeutic benefit. The modest performance of untargeted IL-2 is not surprising, considering the observation that most anticancer agents feature tumor/organ ratios <1, in some cases as low as 1:20 after intravenous injection. (Bosslet K, Straub R, Blumrich M, Czech J, Gerken M, Sperker B, Kroemer H K, Gesson J P, Koch M, Monneret C. Elucidation of the mechanism enabling tumor selective prodrug monotherapy. Cancer Res 1998;58:1195-1201).

This is the first study to prove the therapeutic efficacy of L19IL2 in the context of pancreatic carcinoma. Moreover, we demonstrated for the first time the therapeutic potency of L19IL2 to control metastatic disease, using a pathophysiologically relevant orthotopic mouse model for pancreatic cancer. It is noteworthy that the growth-inhibitory effect of L19IL2 was not cell-type specific, but could be established in two different mouse models of pancreatic cancer, although they exhibit different quantitative levels of ED-B expression.

Furthermore, our data indicate that L19IL2 alone can inhibit pancreatic cancer growth to a greater degree than gemcitabine, a standard first-line chemotherapeutic agent available for the treatment of human pancreatic cancer. Indeed, two applications of L19IL2 were sufficient to reduce the tumor load of mice bearing pancreatic cancer to only 25% of that observed in controls. The clinical promise and scope of L19IL2 therapy was shown by the induction of complete remission and the lack of tumor relapse in 40% of long-term surviving mice bearing pancreatic cancer.

Moreover, surprisingly positive therapeutic results were achieved by treating tumor bearing mice with a combinatorial therapy of L19IL2 plus gemcitabine hydrochloride: a 97% inhibition of primary pancreatic tumor growth, including 70% complete remissions was observed.

The mechanisms underlying the anti-tumor activity of IL-2 are still not fully understood. To address this issue, we performed histological investigations. One of the most intriguing features of L19IL2 treated tumors was extensive tumor necrosis. The degree of necrosis and its location in the central part of tumor tissue where only a scanty leukocyte infiltrate was observed suggest rather other underlying mechanisms than individual tumor cell death caused by direct cell to cell contact by NK cells, macrophages or other immune effector cells. Indeed, recent evidence indicates that IL-2-dependent induction of massive tumor necrosis following local IL-2 administration is due to local vascular leak syndrome, which may be provoked by either lymphocytes and nitric oxide produced by IL-2 activated immune effector cells (De Mik H J, Koten J W, Maas R A, Dullens H F, Den Otter W. Tumour regression by IL-2 mediated stagnation of blood flow. In Vivo 1991;5:679-684; Sakkoula E, Pipili-Synetos E, Maragoudakis M E. Involvement of nitric oxide in the inhibition of angiogenesis by interleukin-2. Br J Pharmacol 1997;122:793-795) and/or by direct cytotoxic effects of IL-2 (Baluna R, Rizo J, Gordon B E, Ghetie V, Vitetta E S. Evidence for a structural motif in toxins and interleukin-2 that may be responsible for binding to endothelial cells and initiating vascular leak syndrome. Proc Natl Acad Sci USA 1999;96:3957-3962) and of activated NK cells on endothelium (Albertsson P A, Basse P H, Hokland M, Goldfarb R H, Nagelkerke J F, Nannmark U, Kuppen P J. NK cells and the tumour microenvironment: implications for NK-cell function and anti-tumour activity. Trends Immunol 2003;24:603-609; Di Carlo E, Meazza R, Basso S, Rosso O, Comes A, Gaggero A, Musiani P, Santi L, Ferrini S. Dissimilar anti-tumour reactions induced by tumour cells engineered with the interleukin-2 or interleukin-15 gene in nude mice. J Pathol 2000;191:193-201). Considering, that endothelial cells migrate along ECM structures containing ED-B FN (Tarli L, Balza E, Viti F, Borsi L, Castellani P, Berndorff D, Dinkelborg L, Neri D, Zardi L. A high-affinity human antibody that targets tumoral blood vessels. Blood 1999;94:192-198) and that IL-2 is selectively delivered to the ECM by linking it to scFv L19, contribution of direct cytotoxic effects of IL-2 on endothelial cells to IL-2 dependent tumor necrosis and regression offers an extremely attractive hypothesis. While IL-2 has been reported to exert cytotoxicity towards endothelial cells, this cytokine has interestingly no direct impact on cancer cells, which can grow unimpeded in vitro in high concentrations of IL-2. (Rosenberg S A. Progress in the development of immunotherapy for the treatment of patients with cancer. J Intern Med 2001;250: 462-475). Nevertheless, tumor samples of mice treated with L19IL2 revealed a considerable decrease in the number of proliferating cells as shown by immunohistochemical analysis for Ki67 expression.

Regarding potential immune effector cells mediating L19IL2 induced tumor regression, we observed a L19IL2 triggered fourfold increase in the number of tumor infiltrating macrophages via immunohistochemistry. This observation is in agreement with the notion that macrophages respond to IL-2 stimulation with tumoridical activity and cytokine and growth factor production. Moreover, it has been established that depletion of macrophages attenuates the therapeutic efficacy of IL-2 (Masztalerz A, Van Rooijen N, Den Otter W, Everse L A. Mechanisms of macrophage cytotoxicity in IL-2 and IL-12 mediated tumour regression. Cancer Immunol Immunother 2003;52:235-242). However, macrophage-depletion was not capable of completely abrogating the anti-tumor activity of IL-2, indicating the contribution of additional mechanisms. In accordance with this concept, a strongly (70 fold) enhanced presence of NK cells was observed in L19IL2 treated tumors in our study. The functional significance of NK cell infiltration into tumor tissues for IL-2 triggered anti-tumor response was corroborated by the observation that NK cell depletion completely abolished the therapeutic effect of L19IL2 against pancreatic cancer. Moreover, our data are supported by the following lines of evidence:

(i) Promising anti-tumor effects in addition to extravasation and infiltration of tumor tissues by NK cells have been demonstrated in vitro and in vivo, (ii) NK cells have been considered the predominantly stimulated leukocytes subpopulation by recombinant IL-2 in preclinical and clinical settings (Basse P H, Whiteside T L, Herberman R B. Use of activated natural killer cells for tumor immunotherapy in mouse and human. Methods Mol Biol 2000;121:81-9;: Janssen R A, Sleijfer D T, Heijn A A, Mulder N H, The TH, de Leij L. Peripheral blood lymphocyte number and phenotype prior to therapy correlate with response in subcutaneously applied rIL-2 therapy of renal cell carcinoma. Br J Cancer 1992;66:1177-1179).

We have therefore established the recombinant fusion protein L19IL2 as a novel, highly efficient and specific anticancer agent for the treatment of pancreatic cancer in orthotopic nude mouse models and characterized underlying immune- and nonimmune-mediated mechanisms.

Moreover, our preclinical data strongly support the initiation of clinical studies using the immunocytokine L19IL2 in pancreatic cancer.

In a preferred embodiment, the fusion protein has a N-terminal antibody-part and C-terminal Interleukin-2 part or wherein the fusion protein has a N-terminal Interleukin-2 part and a C-terminal anti-body-part.

In another preferred embodiment, the fusion protein comprises a linker connecting the antibody-part and the Interleukin-2 part.

Preferably, the antibody-part is human.

In a preferred embodiment, the antibody-part specifically recognising the ED-B domain of fibronectin binds with sub-nanomolar affinity. For a review on the definitions and measurements of anti body-antigen affinity, see Ned et al. (1996). Trends in Biotechnol. 14, 465-470.

In a preferred embodiment, the antibody-part contains at least one of the CDRs of L19 antibody, preferably it contains all CDR sequences of the L19 antibody.

In a preferred embodiment, the antibody-part comprises at least one of the SEQ ID. No. 6 to 11. Preferably, the antibody comprises the sequences according to SEQ ID no. 6 to 11.

In another preferred embodiment, the antibody-part comprises at least one V heavy chain according to Seq. Id. No. 01 or at least one V light chain according to Seq. Id. No. 02. In a more preferred embodiment, the antibody part comprises at least one V heavy chain according to Seq. Id. No. 01 and at least one V light chain according to Seq. Id. No. 02. In an even more preferred embodiment, the antibody-part comprises one V heavy chain according to Seq. Id. No. 01 and one V light chain according to Seq. Id. No. 02.

Preferred is an antibody part, wherein the heavy and the light chain are connected by an antibody linker.

In a preferred embodiment, the antibody linker comprises a sequence according to Seq. Id. No. 03, or a sequence having at least 90% identity to the sequence according to Seq. Id. No. 03. In a more preferred embodiment, the antibody linker has a sequence according to Seq. Id. No. 03.

In a preferred embodiment, the Interleukin-2 part is human Interleukin-2 or a functional variant thereof.

In a more preferred embodiment, the Interleukin-2 part comprises a sequence according to the Seq. Id No 04.

The Interleukin-2 part may be glycosylated or unglycosylated. In case of unglycosylated Interleukin-2, the glycosylation pattern may be identical or different from native human Interleukin-2.

Preferred is the use of the fusion protein according to the invention, wherein the fusion protein linker comprises a sequence according to the Seq. Id No 05, preferably the fusion protein linker has a sequence according to the Seq. Id No 05.

In a preferred embodiment the fusion protein linker has a length of 1 to 30 amino acids, more preferred 4 to 25, even more preferred 6 to 20 amino acids.

In case the antibody-part is in scFv or diabody format, the antibody linker has a length of 1 to 20 amino acids, more preferred 4 to 15, even more preferred 6 to 15 amino acids.

In one embodiment, the fusion protein according to the invention is used as a medicament for treatment of pancreatic cancer.

The fusion protein may be present in monomeric, or multimeric, e.g. homodimeric form in aqueous solution, or mixtures thereof. In a preferred embodiment, the fusion protein is monomeric, or homodimeric or a mixture thereof.

In another embodiment, the anticancer therapy relates to a combination of a fusion protein according to the invention and gemcitabine. The combination is especially useful for cancer therapy.

Preferred is a combination according to the invention.

In a preferred embodiment, the fusion protein has an N-terminal antibody-part and C-terminal Interleukin-2 part or wherein the fusion protein has an N-terminal Interleukin-2 part and an C-terminal antibody-part.

In another preferred embodiment, the fusion protein comprises a linker connecting the antibody-part and the Interleukin-2 part.

Preferably, the antibody-part is human, chimeric or humanized, particularly preferred human.

In a preferred embodiment, the antibody-part specifically recognising the ED-B domain of fibronectin binds with sub-nanomolar affinity. For a review on the definitions and measurements of anti body-antigen affinity, see Ned et al. (1996). Trends in Biotechnol. 14, 465-470.

In a preferred embodiment, the antibody-part contains at least one of the CDRs of L19 antibody, preferably it contains all CDR sequences of the L19 antibody.

In a preferred embodiment, the antibody-part comprises at least one of the SEQ ID. No. 6 to 11. Preferably the antibody comprises the sequences according to SEQ ID no. 6 to 11.

In another preferred embodiment, the antibody-part comprises at least one V heavy chain according to Seq. Id. No. 01 or at least one V light chain according to Seq. Id. No. 02. in a more preferred embodiment, the antibody part comprises at least one least one V heavy chain according to Seq. Id. No. 01 and at least one V light chain according to Seq. Id. No. 02. In an even more preferred embodiment, the antibody-part comprises one V heavy chain according to Seq. Id. No. 01 and one V light chain according to Seq. Id. No. 02.

Preferred is an antibody part, wherein the heavy and the light chain are connected by an antibody linker.

In a preferred embodiment, the antibody linker comprises a sequence according to Seq. Id. No. 03, or a sequence having at least 90% identity to the sequence according to Seq. Id. No. 03. In a more preferred embodiment, the antibody linker has a sequence according to Seq. Id. No. 03.

In a preferred embodiment, the Interleukin-2 part is human Interleukin-2 or a functional variant thereof.

In a more preferred embodiment, the Interleukin-2 part comprises a sequence according to the Seq. Id No 04.

The Interleukin-2 part may be glycosylated or unglycosylated. In case of unglycosylated Interleukin-2 the glycosylation pattern may be identical or different from native human Interleukin-2.

Preferred is the use of the fusion protein according to the invention, wherein the fusion protein linker comprises a sequence according to the Seq. Id No 05, preferably the fusion protein linker has a sequence according to the Seq. Id No 05.

In a preferred embodiment the fusion protein linker has a length of 1 to 30 amino acids, more preferred 4 to 25, even more preferred 6 to 20 amino acids.

In case the antibody-part is in scFv or diabody format, the antibody linker has a length of 1 to 20 amino acids, more preferred 4 to 15, even more preferred 6 to 15 amino acids.

In one embodiment, the fusion protein according to the invention is used as a medicament for treatment of pancreatic cancer in particular pancreatic carcinoma.

Preferred is a combination according to the invention for use as medicament.

More preferred is a combination according to the invention for use as a medicament for treatment of cancer.

In another embodiment, the invention relates to a combination according to the invention, wherein the cancer is selected from non-small cell lung cancer, head and neck cancer, ovarian and breast cancer, preferably pancreatic cancer.

Preferred are combinations with further substances used in cancer therapy.

A combination is a pharmaceutical composition comprising at least two pharmaceutically active compounds. These compounds can be administered simultaneously or separately with a time gap of 1 minute to several days. The compounds can be administered via the same route or differently; e.g. oral administration of one active compound and parenteral administration of another are possible. Also, the active compounds may be formulated in one medicament, e.g. in one infusion solution or as a kit comprising both compounds formulated separately. Also, it is possible that both compounds are present in two or more packages.

A composition comprises at least one pharmaceutically active compound together with pharmaceutically acceptable diluents and/or carriers.

"Specifically recognising" according to the present invention refers to antibody binding to a predetermined antigen. Typically, the antibody binds with an affinity of at least about $1 \times 10^{-7}$ $M^{-1}$, and binds to the predetermined antigen with an affinity that is at least two-fold greater than its affinity for binding to a non-specific antigen (e.g., BSA, casein) other than the predetermined antigen or a closely-related antigen. The antigen is the ED-B domain of fibronectin.

Antibody linker is any linker, preferably a peptide linker, which is suitable for linking Vh and Vl domains. Suitable linkers are for example described in Bird et al, Science, 242, 423-426, 1988; Huston et al, PNAS USA, 85, 5879-5883, 1988, EP 0 573 551; EP 0 623679 and EP 0 318554, which documents are introduced by reference.

Fusion protein linkers are linkers suitable for linking an antibody or antibody-fragment and a second biologically active protein, preferably the linker is peptidic. Suitable linkers are described in EP 0 573 551; EP 0 623679 and EP 0 318554, which documents are introduced by reference. In particular, suitable linkers are described in EP 0 623679.

Interleukin-2 according to the present invention refers to mammalian Interleukin-2, preferably human Interleukin-2 and functional variants thereof. Functional variants of Interleukin-2 are variants of human Interleukin-2 which exhibit at least 10%, but more preferably more than 50%, and even more preferred more than 90% of the activity of native human Interleukin-2. Interleukin-2 activities are activities of Interleukin-2 in biochemical assays or in vivo, in particular Interleukin-2 activity can be measured by the effect on proliferation and/or differentiation of activated T and B lymphocytes and of natural killer cells and/or induction of cytotoxic T cell activity and/or NK/lymphokine activated killer (LAK) antitumour activity. (Meazza R, Marciano S, Sforzini S, et al. Analysis of IL-2 receptor expression and of the biological effects of IL-2 gene transfection in small-cell lung cancer. Br. J. Cancer. 1996; 74:788-795). In particular, functional variants are cystein-125 muteins of Interleukin-2 as described in EP 0109748 and other muteins, including cystein muteins as described in EP136489, in particular serine 125-Interleukin-2. Also, the N-terminus of hIL.2 variants may be altered without significantly affecting the activity, in particular the N-terminal 1-5 amino acids, especially preferred the N-terminal Alanine may be deleted or altered, preferably deleted. Moreover, the Interleukin-2 may contain altered or deleted post-translational modifications, in particular the glycosylation pattern may be altered or missing. Different or absent glycosylation may be obtained e.g. either by mutating the sequence or by expression of the fusion protein in an appropriate host. For example, Aldesleukin, which is approved for metastatic RCC, is unglycosylated des-alanyl-1, serine-125 human interleukine-2 produced in E. coli.

"Antibody-dependent cell-mediated cytotoxicity" and "ADCC" refers to a cell-mediated reaction in which non-specific cytotoxic cells that express Fc receptors (FcRs) (e.g. Natural Killer (NK) cells, neutrophils, and macrophages) recognise bound antibody on a target cell and subsequently cause lysis of the target cell. The primary cells for mediating ADCC, NK cells, express FcγRIII only, whereas monocytes express FcγRI, FcγRII and FcγRIII. FcR expression on haematopoietic cells in summarised is Table 3 on Page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

"Human effector cells" are leukocytes which express one or more FcRs and perform effector functions. Preferably, the cells express at least FcγRIII and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994), and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the foetus (Guyer et al., J. Immunol. 11 7587 (1976) and Kim et al., J. Immunol. 24:249 (1994)).

Antibody—part comprises an antibody as defined below.

The term "antibody" herein is used in the broadest sense and specifically covers intact monoclonal antibodies, polyclonal antibodies, multispecific antibodies (e.g. bispecific antibodies), and antibody fragments so long as they exhibit the desired biological activity. Preferably, the antibody is human, chimeric or humanized, particularly preferred human.

"Antibody fragments" comprise a portion of an intact antibody, preferably comprising the antigen-binding or variable region thereof. Examples of antibody fragments include: Fab, Fab', F(ab')$_2$ and Fv fragments, single chain Fv fragments; diabodies; minibodies, nanobodies, linear antibodies; single-chain antibody molecules; and multispecific anti-bodies formed from antibody fragments. Preferably, the antibody fragment is human, chimeric or humanized, particularly preferred human.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hyper-variable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (See Kabat et al., *Sequences of Proteins Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a Single antigen-binding site, and a residual "Fc" fragment, whose name reflects its ability to crystallize readily. Pepsin treatment yields F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an anti-gen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab'), antibody fragments originally were produced as pairs of Fab'$_2$-fragments which have hinge cysteines between them. Other chemical couplings of antibody fragments are also known.

The "light chains" of antibodies (immunoglobulins) from any vertebrate species can be assigned to one of two clearly distinct types, called kappa (K) and lambda (A), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of antibodies are called α, δ, ε, γ, and μ respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$, domains which enables the scFv to form the desired structure for antigen binding. For a review of scFv See Plückthun in *The Pharmacology of Monoclonal Antibodies*, vol. 113, Rosenburg and Moore eds., Springer-Verlag, New York, pp. 269-315 (1994).

In a further embodiment, antibodies or antibody fragments can be isolated from anti-body phage libraries generated using the techniques described in McCafferty et al., *Nature*, 348552-554 (1990). Clackson et al., *Nature*, 352:624-628 (1991) and Marks et al., *J. Mol. Biol.*, 222581-597 (1991) describe the isolation of murine and human antibodies, respectively, using phage libraries. Subsequent publications describe the production of high affinity (mM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies. The DNA also may be modified, for example, by substituting the coding sequence for human heavy- and light-chain constant domains in place of the homologous murine sequences (U.S. Pat. No. 4,816,567; Morrison, et al., *Proc. Nat. Acad. Sci. USA*, 81:685 1 (1984)), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The term "diabodies" refers to small antibody fragments with two antigen-binding sites. Such fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., *Proc. Natl. Acad. Sci. USA*, 905444-6448 (1993).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal anti-bodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (See, e.g., U.S. Pat. No. 4,816,567).

The "monoclonal antibodies" may also be isolated from phage antibody libraries using the techniques described in Clackson et al., *Nature*, 352:624-628 (1991) and Marks et al., *J. Mol. Biol.*, 222581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:685 1-6855 (1984)).

Chimeric antibodies of interest herein include "primatised" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

Humanised antibodies: Methods for humanising non-human antibodies have been described in the art. Preferably, a humanised antibody has one or more amino acid residues introduced into it from a source which is non-human. These non-human amino acid residues are often referred to as "import" residues, which are typicality taken from an "import" variable domain. Humanisation can be essentially performed following the method of Winter and Co-workers (Jones et al., *Nature*, 321522-525 (1986); Riechmann et al., *Nature*, 332:323-327 (1988); Verhoeyen et al., *Science*, 239: 1534-1536 (1988)), by substituting hypervariable region sequences for the corresponding sequences of a human antibody. Accordingly, such "humanised" antibodies are chimeric antibodies (U.S. Pat. No. 4,816,567) wherein substantially less than an intact human variable domain has been substituted by the corresponding sequence from a non-human species. In practice, humanised antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanised antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanised antibodies (Carter et al., *Proc. Natl. Acad. Sci. USA*, 89:4285 (1992); Presta et al., *J. Immunol.*, 151:2623 (1993)). It is further important that antibodies be humanized with retention of high affinity for the antigen and other favourable biological properties. To achieve this goal, according to a preferred method, humanised antibodies are prepared by a process of analysis of the parental sequences and various conceptual humanised products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences.

Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies: As an alternative to humanisation, human antibodies can be generated. For example, it is now possible to produce transgenic animals (e.g., mice) that are capable, upon immunisation, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous anti-body production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222581-597 (1991), or Griffith et. al., EMBO J. 12:725-734 (1993). See, also, U.S. Pat. Nos. 5,565,332 and 5,573, 905. Human antibodies may also be generated by in vitro activated B cells (see U.S. Pat. Nos. 5,567,610 and 5,229, 275).

The term "hypervariable region" when used herein refers to the amino acid residues of an antibody which are responsible for antigen-binding. The hypervariable region comprises amino acid residues from a "complementarily determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). "Framework" or "FR" residues are those variable domain residues other than the hypervariable region residues as herein defined.

Antibody fragments: Various techniques have been developed for the production of antibody fragments. Traditionally, these fragments were derived via proteolytic digestion of intact antibodies (See, e.g., Morimoto et al., Journal of Biochemical und Biophysical Methods 24: 107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Biotechnology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

The term "specifically recognising" refers to antibody binding to a predetermined anti-gen. Typically, the antibody binds with an affinity of at least $1 \times 10^{-7}$ M, and binds to the ED-B domain of fibronectin that is at least two-fold greater than the affinity for binding to a non-specific antigen (e.g. BSA, casein) other than ED-B domain of fibronectin.

Amino acid sequence modification(s) of protein or Peptide antagonists or antibody-part described herein are contemplated. For example, it may be desirable to improve the binding affinity and/or other biological properties of the antagonist. Amino acid sequence variants of the antagonist are prepared by introducing appropriate nucleotide changes into the antagonist nucleic acid, or by peptide synthesis. Such modifications include, for example, deletions from, and/or insertions into and or substitutions of, residues within the amino acid sequences of the antagonist. Any combination of deletion, insertion, and substitution is made to arrive at the final construct, provided that the final construct possesses the desired characteristics. Therefore, in case of the heavy or light chain, a variation of 1; 2; 3; 4; 5; 6; 7; 8; 9; 10; 11; 12; 13; 14; 15; 16; 17; 18, 19 or 20 amino acids can be executed. In case of Interleukin-2, a variation of 1; 2; 3; 4; 5; 6; 7; 8; 9; 10; 11; 12; 13; 14; 15; 16; 17; 18, 19, 20; 21; 22; 23; 24; 25; 26; 27; 28; 29; 30; 31; 32; or 33 amino acids can be executed. In case of a linker, a variation of 1; 2; 3; 4; 5; 6; or 7 amino acids can be executed. In case of the linker, the variations are much more flexible, because it is simple to create a sufficient space between the functional amino acid sequences. A variation is defined as a deletion, insertion and/or substitution. The amino acid changes also may alter post-translational processes of the antagonist, such as changing the number or position of glycosylation sites. A useful method for identification of certain residues or regions of the antagonist that are preferred locations for mutagenesis is called "alanine scanning mutagenesis" as described by Cunningham and Welk *Science*, 244: 108 1-1085 (1989). Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed antagonist variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist. Another type of variant is an amino acid substitution variant. These variants have at least one amino acid residue in the antagonist molecule replaced by a different residue. The sites of greatest interest for substitutional mutagenesis of antibody antagonists include the hypervariable regions, but FR alterations are also contemplated. Conservative substitutions are shown in Table 1 under the heading of "preferred substitutions".

TABLE 1

| Original Residue | Exemplary substitution | Preferred Substitution |
|---|---|---|
| Ala | Val; Leu; Ile | Val |
| Arg | Lys, Gln, Asn | Lys |
| Asn | Gln, His, Asp, Lys, Arg | Gln |
| Asp | Glu, Asn | Glu |
| Cys | Ser, Ala | Ser |
| Gln | Asn, Glu | Asn |
| Glu | Asp, Gln, | Asp |
| Gly | Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile, | Leu |
| Phe | Leu, Val, Ile, Ala, Tyr | Tyr |
| Pro | Ala | Ala |
| Ser | Thr | Thr |
| Thr | Ser | Ser |
| Trp | Tyr, Phe | Tyr |
| Tyr | Trp, Phe, Thr, Ser | Phe |
| Val | Ile, Leu, Met, Phe, Ala, Norleucine | Leu |

If such substitutions result in a change in biological activity, then more substantial changes, denominated "exemplary substitutions" in Table 1, or as further described below in reference to amino acid classes, may be introduced and the products screened.

Substantial modifications in the biological properties of the antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Non-conservative substitutions will entail exchanging a member of one of these classes for another class. Any cysteine residue not involved in maintaining the proper conformation of the antagonist also may be substituted, generally with serine, to improve the oxidative stability of the molecule and prevent aberrant cross linking. Conversely, cysteine bond(s) may be added to the antagonist to improve its stability (particularly where the antagonist is an antibody fragment such as a Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hyper-variable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyse a crystal structure of the antigen-antibody complex to identify contact points between antibody and anti-gen. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antagonist alters the original glycosylation pattern of the antagonist. By altering it is meant to delete one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antagonist is conveniently accomplished by altering the amino acid sequence such that it contains one or more of the above-described tri-peptide sequences (for N-linked glycosylation sites). The alteration may also be made by the addition of, or substitution by, one or more serine or threonine residues to the sequence of the original antagonist (for O-linked glycosylation sites).

Nucleic acid molecules encoding amino acid sequence variants of the antagonist are pre-pared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antagonist of the invention with respect to effector function, e.g. so as to enhance antigen-dependent cell-mediated cyotoxicity (ADCC) and/or complement dependent cytotoxicity (CDC) of the antagonist. This may be achieved by introducing one or more amino acid substitutions in an Fc region of an anti-body antagonist. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumour activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

In a preferred embodiment of the invention, L19IL2 is used according to the invention, which comprises the sequences according to SEQ ID. No 4.

In a preferred embodiment of the invention, L19IL2 is used according to the invention, which comprises the sequences according to SEQ ID. No 6 to 11.

In a preferred embodiment of the invention, L19IL2 is used according to the invention, which comprises the sequences according to SEQ ID. No. 1, 2, 3, 4, and 5.

In another embodiment of the invention the L19IL2 fusion protein contains variations compared to the sequences according to SEQ ID. No. 1, 2, 3, 4, and 5. Variations of the fusion protein L19IL2 are defined by variations as mentioned before. In particular, amino acids in the L19IL2 molecule may be modified according to Table 2, by deletion, insertion and/or substitution of amino acids compared to those defined by SEQ ID. No. 1, 2, 3, 4, and 5:

TABLE 2

| Seq. Id No | Type | Numbers of amino acids, which may be deleted, inserted and/or substituted compared to SEQ ID. No. 1, 2, 3, 4, and 5. |
|---|---|---|
| Seq. Id No 1 | VH | 1, 2, 3, 4, 5, 6, 7, 8, 9, 10, 11, 12, 13, 14, 15, 16, 17, 18 |
| Seq. Id No 2 | VL | 1, 2, 3, 4, 5, 6, 7, 8, 9, 10, 11, 12, 13, 14, 15, 16, 17, 18 |
| Seq. Id No 3 | mAb linker | 1, 2, 3, 4, 5, 6, 7 |
| Seq. Id No 4 | IL-2 | 1, 2 ,3, 4, 5, 6, 7, 8, 9, 10, 11, 12, 13, 14, 15, 16 17, 18, 19, 20, 21, 22, 23, 24, 25, 26, 27, 28, 29, 30 |
| Seq. Id No 5 | Fusion protein linker | 1, 2, 3, 4, 5, 6, 7, |

Further modifications are mentioned in Pini et al. (1998) J. Biol. Chem., Vol.: 273, pages 21769-21776, WO 02/20563, WO 2005/37312, and WO 99/58570.

Use as a Medicament Suitable for Therapeutic Intervention

The combination of the invention exhibits pharmacological activity. In particular, the combination shows pharmacological activity in a number of pathological or disease states in connection with a cancer, especially pancreatic cancer.

The combination of the invention is therefore indicated for use in treatment of non-small cell lung cancer, head and neck cancer, colon, ovarian and breast cancer, especially pancreatic cancer. The fusion protein and gemcitabine may be administered simultaneously or separately, at different times.

For the treatment of such conditions, the appropriate dose will, of course, vary depending upon, for example, the host, the mode of administration and the nature and severity of the condition being treated.

In general, an indicated repeat dose of the fusion protein L19IL2 in man is in the range of about 1-100 Mio IL-2 equivalent IU as a fixed dose, preferred 5-30 Mio IL-2 equivalent IU as a fixed dose per application. The antibody must be given in a dose that does not cause toxicity of the most sensitive organ in the body (dose limiting organ). For antibodies, the kidney might be the dose limiting organ and impact on the cardiovascular system might be dose-limiting for L19IL2.

Specific binding members of the present invention, including those comprising an anti-body antigen-binding domain, may be administered to a patient in need of treatment via any suitable route, usually by infusion into the bloodstream and/ or directly into the site to be treated, e.g. tumor. The precise dose will depend upon a number of factors, the route of treatment, the size and location of the area to be treated (e.g. tumour), the precise nature of the antibody (e.g. whole antibody, scFv molecule), and the nature of any detectable label or other molecule attached to the antibody. Treatments may be repeated at daily, twice-weekly, weekly or monthly intervals, at the discretion of the physician.

The dose of gemcitabine administered will vary according to the mode of use and route of use, as well as to the requirements of the patient. In general, a weekly application is preferred over a daily dosing for a systemic therapy of adult patients. For the most commonly applied once-weekly schedule the standard dose for gemcitabine is 1000-1250 mg/m$^2$ as an intravenous infusion over 15 to 30 minutes.

The invention discloses in embodiments:

(α) the use of L19IL2 or its combination with gemcitabine for the manufacture of a medicament for treatment of cancer especially non-small cell lung cancer, head and neck cancer, colon, ovarian and breast cancer, in particular pancreatic cancer;

(β) a method of treatment of cancer especially non-small cell lung cancer, head and neck cancer, colon, ovarian and breast cancer, especially pancreatic cancer, which method comprises an administration of a pharmaceutical composition of L19IL2 in combination with gemcitabine, wherein the amount of combination suppresses the disease and wherein the pharmaceutical composition of the combination is given to a patient, who is in need thereof;

(γ) a pharmaceutical composition comprising L19IL2 and gemcitabine.

The preferred method of administration is parenteral, in particular intravenous infusion.

EXAMPLES

IL-2 is one of the most potent known anti-tumor cytokines. However, the efficacy of systemically applied IL-2 has been offset by accompanying toxicities. (Bubenik J, Den Otter W, Huland E. Local cytokine therapy of cancer: interleukin-2, interferons and related cytokines. Cancer Immunol Immunother 2000;49:116-122; Baluna R, Rizo J, Gordon B E, Ghetie V, Vitetta E S. Evidence for a structural motif in toxins and interleukin-2 that may be responsible for binding to endothelial cells and initiating vascular leak syndrome. Proc Natl Acad Sci USA 1999;96:3957-3962). As a result potential effort has been captured in the development of locoregional IL-2 treatment protocols. Recently, local IL-2 treatment of patients with advanced pancreatic cancer via arterial or portal venous catheters in combination with poly-chemotherapy has shown encouraging results yielding an increase of response rates, reduction of tumor load and prolongation of survival time (Abdel-Wahab M, El Shennawy F, Agha S, Ragab E, Fathi O, Sultan A, Elghawalby N, Ezzat F. Evaluation of cell mediated immunity in advanced pancreatic carcinoma before and after treatment with interleukin-2 (IL-2). Hepatogastroenterology 1999;46 Suppl 1:1293-1296; Lygidakis N J, Vlachos L, Raptis S, Sgourakis G, Mourikis D, Kehagias D. Consecutive re-explorations for final resection of initially unresectable pancreatic head carcinoma. Hepatogastroenterology 1999;46:2229-2239). In this context, the selective antibody based delivery of IL-2 to pancreatic cancer represents an appealing approach, because it would achieve the purpose of specifically accumulating IL-2 to the tumor, controlling likewise primary and disseminated tumors while limiting systemic toxicity. In this study, we investigate the therapeutic efficacy of the recombinant fusion protein L19IL2 in pancreatic cancer.

Materials and Methods

Materials

The following were purchased: human pancreatic carcinoma cell lines MiaPaca (American Type Culture Collection) and DanG and murine lymphoma cell line YAC-1 (Deutsche Sammlung von Mikroorganismen und Zellkulturen (DSMZ) GmbH, Braun-schweig, Germany); Dulbecco's Eagle medium (DMEM), RPMI 1640 medium, PBS, Hanks' Balanced Salt Solution (HBSS), Antibiotic/Antimycotic Solution, glutamine and hygromycin B (Invitrogen, Berlin, Germany); fetal calf serum (FCS), trypsin/EDTA, penicillin, and streptomycin (Biochrom, Berlin, Germany); human fusion protein L19IL2 and human homodimeric scFv antibody fragment L19 (Schering A G, Berlin, Germany); Ficoll-Paque Plus (Amersham, Braunschweig, Germany); collagenase Type 3 (Worthington, N.J., USA); AmpliTaq Gold DNA polymerase (Applied Biosystems, CA, USA); PCR Nucleotide Mix (Roche Diagnostics, Indianapolis, USA); TumorTACS in situ Apoptosis Detection Kit (R&D Systems GmbH, Wiesbaden-Nordenstadt, Germany); monoclonal mouse anti-human-pancytokeratin (C11) Ab (Santa Cruz Biotechnology, CA, USA); monoclonal mouse anti-human Ki67 Ab (Dianova, Hamburg, Germany); Biotin conjugated monoclonal mouse anti mouse NK 1.1 (PK136) Ab (Serotec, Düsseldorf Germany), monoclonal rat anti mouse CD11b (M1/70) Ab and R-PE conjugated monoclonal rat anti mouse CD49b (DX5) Ab (BDBiosciences, Heidelberg, Germany); rabbit anti asialo GM1 antiserum (ASGM1) (Wako Chemicals GmbH, Neuss, Germany); monoclonal mouse anti human CD31 (JC/70A) Ab, monoclonal mouse anti human CA 19-9 (1116-NS-19-9) Ab and AEC-Substrate-Chromogen (Dako, Hamburg, Germany); Vectastain ABC kit (Vector Laboratories, Wertheim-Bettingen, Germany); Alamar Blue (BioSource, CA, USA); QIAamp DNA Mini Kit (Qiagen, Hilden, Germany); gemcitabine (Lilly, Gießen, Germany), Rompun 2% (Bayer GmbH, Leverkusen, Germany); Ketavet (Pharmacia GmbH, Erlangen, Germany). All other chemicals and reagents were purchased from Sigma Chemical Co. (Deisenhofen, Germany).

Human Tissue Samples 21 pancreatic carcinoma, 17 chronic pancreatitis and 13 normal pancreatic tissue samples were obtained from individuals who underwent surgical resection at the Department of Surgery at Charité University Hospital. This study was approved by the local ethics committee and all patients gave written informed consent prior to surgery.

Cell Culture

The human pancreatic carcinoma cell lines DAN-G and MiaPaca and the murine lymphoma cell line YAC-1 were cultured as previously described. (Wagner K, Scholz A, Wiedenmann Bertram and Menrad Andreas, The targeted immunocytokine L19IL2 efficiently inhibits the growth of orthotopic cancer in nude mice, paper submitted to Cancer Research). MiaPaca cells, stably transfected with an Angiopoetin 2 DNA construct, were maintained as MiaPaca wild type cells, except for the addition of hygromycine B at a concentration of 300 µg/ml.

Animals

Female NMRI nude mice (age, approx. 10 weeks; weight 21-25 g) were purchased from Bomholtgard (Ry, Denmark). Animal care followed institutional guidelines and all experiments were approved by local animal research authorities.

Tumor Implantation and in vivo Treatment

Three orthotopic xenograft mouse models of pancreatic carcinoma were established, including two non-metastatic models by injection of wild type cells of the human pancreatic carcinoma cell lines DanG and MiaPaca, and one metastatic model by implantation of MiaPaca cells stably transfected with an Angiopoetin 2 DNA construct (MiaPaca-A2) (established by A. Scholz, unpublished data). Orthotopic transplantation was carried out as described. (Alves F, Contag S, Missbach M, Kaspareit J, Nebendahl K, Borchers U, Heidrick B, Streich R, Hiddemann W, An orthotopic model of ductal adenocarcinoma of the pancreas in severe combined immunodeficient mice representing all steps of the metastatic cascade. Pancreas 2001; 23:227-235). In brief, mice were anesthetized by intraperitoneally (i.p.) administering a mixture of ketamine (100 mg/kg) and xylazine (10 mg/kg). After median laparotomy, the peritoneum was opened, and the pancreas was exposed. Aliquots of $1 \times 10^6$ tumor cells in a volume of 10/µl PBS were injected with an insulin syringe into the head of the pancreas to visibly infiltrate the pancreatic tissue. The pancreas was placed back to its original position and the abdominal wall was closed in two layers using Vicryl 6-0 for the peritoneum and suture clips for the skin. Before initiation of therapy, 10 mice were killed to confirm the presence of tumor lesions. Mice were randomised and groups of 10-12 mice were intravenously (i.v.) treated with vehicle (0.9% saline), untargeted IL-2, homodimeric scFv L19 or L19-IL-2, consisting of IL-2 conjugated to the homodimeric scFv L19 or i.p. administered together with gemcitabine according to different protocols as described in the results section. All therapeutic agents were diluted in 0.9% saline and applied in a volume of 1/µl/g BW. After termination of therapy, mice were killed, blood samples were collected and tumor volume was calculated using the formula length×width×depth×π/6. The area of lymph nodes of the metastatic MiaPac-A2 tumor model was calculated by determining the largest diameter and its perpendicular diameter and computing the product of the two measurements. In one experiment, mice were kept alive after completion of therapy to obtain long term data. At the end of therapy and biweekly thereafter, mouse blood samples were taken by retroorbital bleeding with heparinized blood collection capillaries to assay serum CA 19-9 levels. Survival time of mice was followed until day 100 after cessation of therapy (day 121 after tumor cell transplantation). Mice were considered to be cured if there was no detectable tumor at day 100.

Depletion of Natural Killer (NK) Cells

NK cell depletion was performed as previously described. (Peron J M, Couderc B, Rochaix P, Douin-Echinard V, Asnacious A, Souque A, Voigt J J, Bus ail L, Vine J P, Favre G, Treatment of murine hepatocellular carcinoma using genetically modified cells to express interleukin-12. J Gastroenterology Hepatic 2004; 19:388-396.) Briefly, mice were injected i.p. with 50/µl anti asialo-GM-1 (ASGM1) Ab 3 days before tumor cell injection and every 4 days for a total of 6 injections. Quality of NK cell depletion was monitored by flow cytometry and cytotoxicity assay.

Preparation of Spleen Mononuclear Cells (MNC)

Mononuclear cells were prepared from the spleens of mice depleted for NK cells or not as described elsewhere. Briefly, spleens were removed under deep general anesthesia and digested with collagenase for 1/hour at 37° C. Subsequently, contents were forced through a 100 µm cell strainer and washed twice with HBSS. Mononuclear cells were separated from the cell suspension by running a Ficoll-Hypaque density gradient centrifugation.

AlamarBlue Cytotoxicity Assay

Cytotoxic activity of isolated murine spleen MNC against YAC-1 cells was examined using a 24-hour alamarBlue cytotoxicity assay as detailed previously.[22]

Flow Cytometry

1×10$^6$ spleen MNC isolated from mice depleted for NK cells or not were incubated with 1 µg PE-labeled anti NK 1.1 antibody for 15 min at 4° C. After washing with PBS, the presence of fluorescence positive cells was analyzed by FACScan utilizing Cellquest software (BectonDickensen; Heidelberg, Germany).

Immunohistochemical Analysis

Surgically resected human and murine tissue samples were snap-frozen in liquid nitrogen and after fixation in PFA 4%, pH 7 for 20 minutes, 4 µm cryostat sections of the frozen tissue were analyzed immunohistochemically using the avidin-biotin-technique as described previously. Slides were incubated for 1 hour with the following primary antibodies: biotinylated L19IL2 (30 µg/ml), monoclonal mouse anti-human CD31 at a 1:100 dilution, rat anti-mouse CD11b at a 1:50 dilution, biotinylated mouse anti-mouse CD161b/c/NK1.1 at a 1:50 dilution, biotinylated mouse anti-human pancytokeratin at a 1:50 dilution. Sections stained with PBS instead of the primary antibody were used as a negative control. Proliferating cells were detected with a monoclonal mouse anti human Ki67 Ab applying the Animal Research Kit. Apoptotic cells were proven by Terminal deoxynucleotidyl transferase mediated dUTP nick end labeling (TUNEL) assay using TumorTACS in situ Apoptosis Detection Kit. Both procedures were carried out following the manufacturer's instructions except that 3-amino-9-ethylcarbazole (AEC) was used as the substrate-chromogen. Negative controls were included by omitting the primary antibody (Animal Research Kit) or the terminal deoxynucleotidyl transferase (TUNEL). Quantitative immunohistochemical analysis for the area of vital (non-necrotic) tumor tissue was carried out by computer aided imaging analysis using Axiovision 4.2 software (Zeiss, Jena, Germany). For quantification of proliferating, apoptotic and inflammatory cells, 20 randomly selected measurement areas (680×510 µm, magnification×20) of each tumor specimen were analyzed and for evaluation of ED-B FN expression, 10 areas (1390/×/1000 µm, magnification×10) were scanned. The results represent the positive staining as a percentage of measurement area (inflammatory cells, ED-B FN) or the ratio of positive tumor cells as a percentage of total tumor cells (Ki67, TUNEL), respectively. For quantitative analysis of necrotic tumor area H&E sections were scanned at low power (×2.5). Total and necrotic tumor area was marked on the screen and areas were calculated by the image analysis system, and the ratio tumor necrosis area/total tumor area was given in percentages.

Extraction of DNA and DNA Polymerase Chain Reaction (PCR)

Genomic DNA of mouse lymph nodes was extracted using the QIAamp DNA Mini Kit according to the manufacturer's recommended protocol. The presence of human specific DNA was proven by polymerase chain reaction (PCR) amplifying an 850 bp fragment of the α-satellite region of the human chromosome 17 using the forward primer 5'-gg-gataatttcagctgactaacacg-3' and the reverse primer 5'-ttccgtt-tagttaggtgcagttatc-3' according to the protocol reported by Becker et al. (Becker M, Nitsche A, Neumann C, Aumann J, Junghahn I, fichtner I, Sensitive PCR method for the detection and real time quantification of human cells in xenotransplantation systems. Br J Cancer 2002;87:1328-1335).

Serum Parameters

Mouse blood samples were obtained by retroorbital bleeding or decapitation. Samples were centrifuged and supernatants were stored at −20° C. Serum CA 19-9 levels were measured by a fully automated chemiluminescence immunoassay on an ADVIA Centaur (Bayer, Leverkusen, Germany) and eipase levels were determined using a kinetic colorimetric assay on an ADVIA 2400 (Bayer, Leverkusen, Germany).

Statistical Analysis

Statistical differences were evaluated by two-sided Mann-Whitney U-test and Fishers exact test and correlation was assessed by linear regression using GraphPad statistical software (GraphPad Software Inc., San Diego, Calif.). Differences were considered statistically significant at p<0.05.

Results

ED-B FN is Selectively Overexpressed in Human Pancreatic Carcinoma

To evaluate the postulated role of ED-B FN as a suitable target for the selective delivery of IL-2 to pancreatic cancer, we initially studied the expression pattern of ED-B FN in human non-transformed pancreatic tissue, chronic pancreatitis, and ductal adenocarcinoma. In parallel, serial sections from the same tissues were stained with a monoclonal antibody against the endothelial cell specific antigen CD31. All but one carcinoma sample analyzed (n=19) revealed an accumulation of ED-B FN at the abluminal site of tumor blood vessels and in the tumor stroma. Quantification of ED-B FN expression in pancreatic cancer revealed a median ED-B FN level of 7.35%±1.60% (FIG. 1B). By contrast, blood vessels and stroma of non-transformed pancreatic tissues (n=11) and chronic pancreatitis (n=15) showed negligible or no ED-B FN expression, corresponding to an ED-B FN ratio below 0.1%, respectively (FIG. 1B). Thus, these data confirm a selective overexpression of ED-B FN in pancreatic carcinoma, thereby laying the groundwork for an ED-B FN based targeted therapy for pancreatic cancer.

To address the therapeutic efficacy of L19IL2 in pancreatic cancer, we sought to establish a suitable mouse model and orthotopically injected the human pancreatic carcinoma cell lines DanG and MiaPaca into the pancreas of nude mice. Immunohistochemical analysis of the resulting orthotopic pancreatic tumors for the expression pattern of ED-B FN consistently revealed a strong immunostaining around tumoral blood vessels and in the stromal compartment. In comparison with the human situation, the quantitative level of ED-B FN was significantly higher in DanG tumors (22.33%±0.65%), but otherwise analogous in MiaPaca tumors (7.96%±1.32%) (FIG. 1B). Verification of qualitative and quantitative ED-B FN expression mimicked the human in vivo situation and allowed us to evaluate the therapeutic impact of L19IL2 on pancreatic carcinoma.

L19IL2 Exerts Significant Anti-tumor Activity Against Established Pancreatic Cancer To determine the efficacy of L19IL2 treatment in a pancreatic cancer situation, athymic nude mice were orthotopically injected with the human pancreatic cancer cell line DanG. After establishment of solid tumors, mice were randomized to receive 0.9% saline or 1.43 MIU/kg BW or 4.29 MIU/kg BW IL-2 equivalents of either L19IL2 or untargeted IL-2 for 10 days. At the end of therapy, all mice were sacrificed and the tumor volume was calculated. While IL-2 treatment had no effect on tumor growth in the lower dose and only a minor effect in the higher dose, administration of L19IL2 resulted in a statistically significant reduction of tumor volume to 21.4% (1.43 MIU/kg BW) and 2.7% (4.29 MIU/kg BW) of that observed in control mice, thus being significantly superior to untargeted IL-2 (FIG. 2A, left panel). In a separate experiment, we sought to rule out IL-2 independent anti-tumor activity of the scFv L19 antibody fragment itself. For this purpose mice were treated with either 4.29 MIU/kg BW L19IL2 or equimolar amounts of scFv L19 alone for 10 days. In accordance with our first experiment, administration of L19IL2 reproducibly led to a statistically significant decrease of tumor load compared to control mice. By contrast, scFv L19 failed to achieve any growth inhibitory effect, underscoring the role of IL-2 as the therapeutically active effector moiety (FIG. 2A, right panel). As a continuous evaluation of tumor size by caliper measurements is not feasible for orthotopically injected tumors, we aimed at establishing a suitable serum marker to monitor tumor progression as well as therapeutic effects on tumor growth and were able to demonstrate a significant correlation between tumor volume and serum concentrations of CA 19-9 (n=56; p<0.0001) (FIG. 2B, left panel). Accordingly and in agreement with the L19IL2 induced reduction of tumor burden described above, administration of L19IL2 resulted in a significant decrease of serum CA 19-9 levels in tumor bearing mice, while IL-2 did not impinge on serum tumor markers (data not shown). Based on this observation, we evaluated the time-response relationship of L19IL2 induced tumor growth delay by repeatedly collecting blood samples of vehicle and L19IL2 treated mice. Interestingly, a L19IL2 dependent tumor growth delay in terms of two fold lower serum CA 19-9 levels when compared to controls was observed as early as day three after start of treatment and this difference continued to increase until the end of the experiment. In fact, at this time point a more than fifteen fold increase in serum CA 19-9 levels was detectable in the control group, whereas serum tumor markers of mice obtaining L19IL2 did not differ significantly from baseline at start of therapy (FIG. 2B, right panel). Having proven the therapeutic impact of L19-IL-2, we next sought to ensure that IL-2 activity and subsequent inflammatory response is confined to the tumor not provoking an acute pancreatitis in adjacent non-transformed pancreatic tissue. For this purpose, mice treated with saline or either targeted or untargeted IL-2 were assayed for serum lipase levels as a surrogate marker of pancreatitis. However, compared to controls, neither L19IL2 nor untargeted IL-2 interfered with serum lipase concentrations (FIG. 2C). This finding was further corroborated by histological analysis of pancreatic tumors and residual non-transformed pancreatic tissues of animals treated with L19IL2 using conventional HE staining and immunostaining with antibodies directed against NK 1.1 (natural killer (NK) cells) and CD11b (predominantly macrophages), respectively. Of note, no signs of acute pancreatitis were detectable and inflammatory cells selectively accumulated in the tumor, sparing out adjacent non-transformed pancreatic tissue, thereby ruling out pancreatitis as an adverse effect of L19IL2 treatment (data not shown).

To investigate whether L19IL2 induced reduction of tumor growth is cell-type specific, mice were orthotopically injected with the human pancreatic cancer cell line MiaPaca. After establishment of solid tumors, mice were randomized to receive 0.9% saline or 1.43MIU/kg BW or 4.29 MIU/kg BW IL-2 equivalents of either L19IL2 or IL-2 for 10 days. While untargeted IL-2 was not therapeutic at low dosage, equimolar amounts of L19IL2 reproducibly led to a significant reduction of tumor load to 10.4% of control (p=0.0003), thereby being significantly (8 fold) superior to untargeted IL-2 (p=0.0003). At high dosage, untargeted IL-2 yielded a significant decrease of tumor volume to 47.3% (p=0.0205) of control. However, application of equimolar amounts of L19IL2 achieved an inhibition of tumor growth to 16.8% of control (p=0.0007), thus being 3 fold more effective than untargeted IL-2, although this difference did not reach statistical significance (p=0.0513) (FIG. 2D).

L19IL2 Significantly Reduces or Eliminates Established Metastases of Pancreatic Cancer Having proven efficacy of L19IL2 for treatment of primary pancreatic tumors, we next explored its potency in metastatic disease. Therefore, mice were orthotopically engrafted with MiaPaca cells, stably transfected with an Ang2 DNA construct (MiaPaca-A2), re-suiting in a metastatic spread of pancreatic cancer to intraabdominal lymph nodes and liver. Metastases were verified by immunohistochemical staining for human pancytokeratin and subsequently investigated for ED-B FN expression. Consistently, all lymph nodes were infiltrated by neoplastic cells and all liver metastases showed immunoreactivity for ED-B FN, whereas non-infiltrated lymph nodes and the liver did not. Based on this observation, mice bearing orthotopic MiaPaca-A2 pancreatic tumors with pre-established lymph node metastases, were randomly treated with vehicle or L19IL2 at 4.29 MIU/kg BW for 10 days (days 60-64 and 67-71). At the end of therapy, all mice were sacrificed and the primary tumor volume as well as the lymph node area was calculated. Besides a significant reduction of primary tumor volume, L19IL2 resulted in a considerable decrease of the median lymph node area to less than 20% of that observed in vehicle-treated controls (p=0.0120) (FIG. 3D, pale bars). Verification of lymph node metastases by immunostaining for pancytokeratin revealed large, polymorphnuclear cells with strong immunoreactivity for cytokeratin in lymph nodes of 80% of control is mice compared to 20% of L19IL2 treated mice. However, most lymph nodes of L19IL2 treated mice displayed small, granulocyte like cells positive for cytokeratin, suggesting cross-reaction of anti-cytokeratin antibodies with granule associated epitopes in granulocytes, which has been reported previously (Streicher J, Fabian B, Herkner K, Pointner H, Bayer P M. Anticytokeratins are a potential source of false-positive indirect immunofluorescence assays for C-ANCA. J Clin Lab Anal 1998; 12:54-59). To further clarify whether these granulocyte-like, but cytokeratin-positive cells represent neoplastic or inflammatory cells, lymph nodes were screened for infiltration of human cancer cells by performing a DNA-PCR for detection of a human specific 850-bp fragment on the α-satellite DNA on human chromosome 17. PCR amplificates of the expected size were detectable in lymph nodes of all positive control mice, but in only 33% of L19IL2 treated mice. Thus, L19IL2 treatment resulted in a significant reduction of lymph node metastases. (P=0.0275) (FIG. 3D, dark bars).

Schedule Dependent Anti-tumor Effects of L19-IL-2

For evaluation of schedule-dependent anti-tumor activity of L19-IL-2, mice orthotopically injected with DanG cells were randomly assigned to control group or treatment with 4.29 MIU/kg BW L19IL2 according to the following protocols (a) once weekly, on days 7, 14; (b) thrice weekly, on days 7, 9, 11, 14, 16, 18; (c) five times by the week, on days 7-11 and 14-18 (FIG. 4, left panel). Compared to controls, all regimens resulted in a significant tumor growth delay. However, application of L19IL2 on days 7-11, 14-18 produced the best tumor response, resulting in a reduction of tumor load to 12% of that observed in controls, whereas decreasing numbers of L19IL2 injections were associated with a decrease in tumor response, although these differences did not reach statistical significance (FIG. 4, right panel).

L19IL2 Treatment Yields Considerable Long-term Effects

Figure 5:
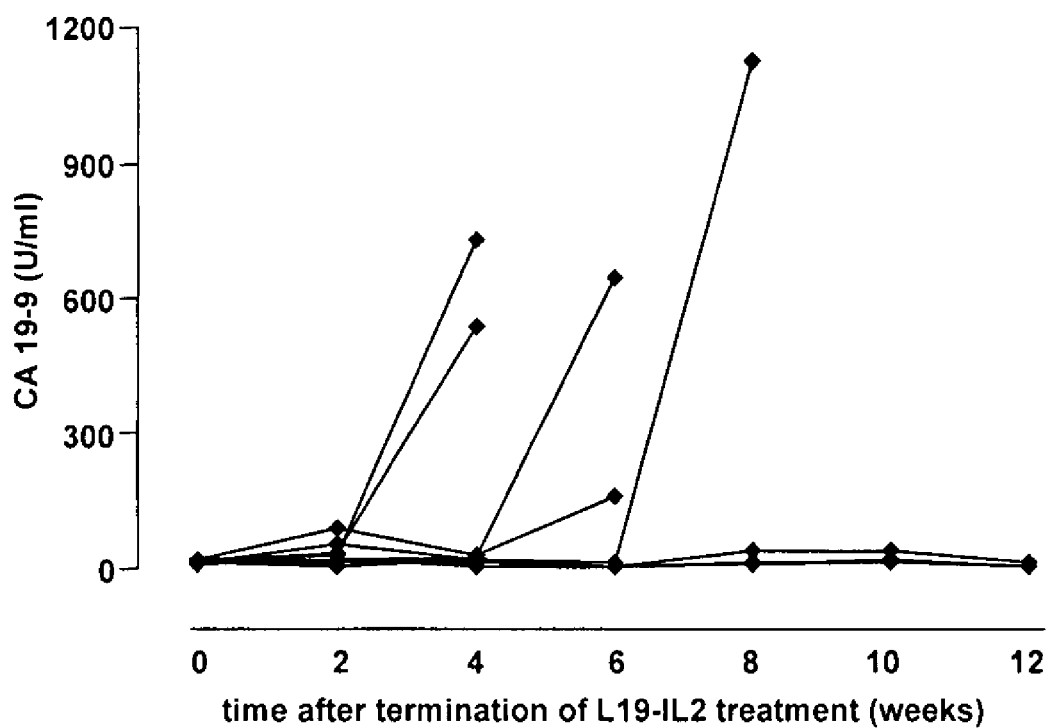

To explore whether L19IL2 is capable to achieve sustainable long term remission, mice bearing orthotopic DanG pancreatic cancer were treated with 4.29 MIU/kg BW L19IL2 for 10 days (days 7-11 and 14-18). Subsequently, mice were left untreated and tumor relapse was monitored by biweekly evaluation of serum CA 19-9 levels. Between the fourth and the eighth week after termination of therapy, six out of 10 mice experienced a marked elevation of serum tumor marker associated with tumor relapse and subsequently died due to tumor burden. One animal developed a dermal tumor without any increase of serum CA 19-9 level. Four out of 10 mice survived without boost of serum CA 19-9 levels throughout the observation period of three months after cessation of therapy. Autopsy preformed at this time point consistently revealed no evidence of tumor recurrence, and animals were considered to be cured (FIG. 5).

Figure 6:
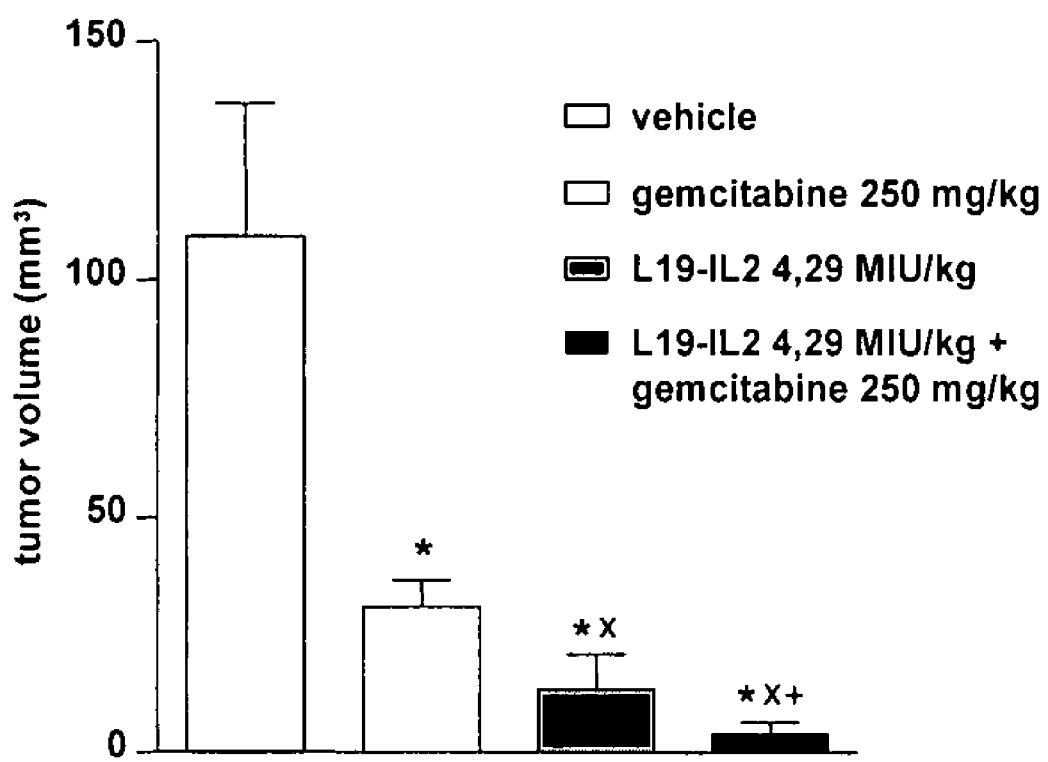

Therapeutic Effect of L19-IL-2, Gemcitabine and a Combination thereof on Pancreatic Cancer Gemcitabine is considered the best currently available cytotoxic drug for treating pancreatic cancer. We therefore compared L19IL2 treatment to gemcitabine and assessed whether a combinatorial treatment of these two agents may yield any therapeutical benefit. For this purpose, standard pancreatic cancer treatment of mice bearing orthotopic DanG tumors with gemcitabine (i.p. injection of 250 mg/kg BW once weekly, i.e. on day 7 and 14) resulted in a significant reduction of pancreatic tumor volume to 28% as compared to control mice. Of note, L19IL2 treatment (i.v. injection of 4.29 MIU/kg BW on days 8-12 and 15-19) alone reduced tumor volume 2.3 fold more than gemcitabine therapy (p=0.0095). Furthermore, when L19IL2 treatment and gemcitabine were combined, tumors were very small, corresponding to a diminution of tumor load to only 12.4% of that observed with gemcitabine treatment (p=0.0004) and 28.53% of that observed with L19IL2 treatment (p=0.0435), respectively (FIG. 6). Moreover, while no complete remission was achieved by treatment with gemcitabine alone, 37% of mice administered with L19IL2 and 70% of mice receiving a combination of L19IL2 plus gemcitabine experienced complete remission.

Effects of L19IL2 on Tumor Necrosis, Apoptosis and Proliferation

To identify the mechanisms underlying L19IL2 induced tumor regression we initially analyzed tumor samples of vehicle and L19IL2 treated mice by conventional H&E staining using the orthotopic DanG pancreatic cancer model as a representative model. One of the most intriguing features of L19IL2 treated tumors was extensive tumor necrosis. Indeed, in mice, receiving L19-IL-2, necrosis comprised 42±10.86% of the tumor area whereas in untreated controls only 2.5±2.177% of the tumor area was necrotic (p=0.0159) (FIG. 7A). Analysis of residual vital tumor tissue for apoptosis via TUNEL assay revealed no relevant difference of apoptotic cell index in tumors of L19IL2 treated mice as compared to vehicle treated controls (FIG. 7B). By contrast, analysis for proliferating cells by Ki67 immunostaining demonstrated that the ratio of dividing cells was substantially (4.6 fold) reduced in tumors of mice administered with L19IL2 in comparison with untreated controls (p=0.0177) (FIG. 7C).

Identification of the Immune Effector Cells Mediating L19IL2 Induced Anti-tumor Response Besides extensive tumor necrosis, H&E staining of L19IL2 treated tumors demonstrated a substantial round cell inflammatory infiltrate which was not detectable in untreated controls. To further identify the immune effector cells mediating L19IL2 induced tumor growth inhibition, tumor specimens were immunohistologically assessed for CD11b+ cells, which predominantly include macrophages and for NK cells. Indeed, a more than four fold enhanced number of CD11b+ cells was detectable in tumors of L19IL2 treated animals as compared to untreated controls (p=0.0012) (FIG. 8A), and— even more striking—a more than 70 fold increase in NK cell infiltration was demonstrated (FIG. 8B), suggesting that NK cells are major players of the L19IL-2 induced anti-tumor response. To further substantiate the suspected role of NK cells, we tested whether NK cell depletion via an anti ASGM-1 antibody interfered with the therapeutic efficacy of L19-IL-2. For this purpose, mice orthotopically engrafted with DanG cells, were randomly assigned to the following treatment groups: NK competent+saline treatment, NK deficient+saline treatment, NK deficient+L19IL2 treatment (4.29 MIU/kg BW L19 on days 7-11, 14-18) and NK competent+L19IL2 treatment (4.29 MIU/kg BW L19 on days 7-11, 14-18). In agreement with our immunohistologic data, L19IL2 treatment did not yield any significant tumor regression in NK deficient mice as compared to NK deficient or NK competent vehicle treated mice. Moreover, L19IL2 was more than 5 fold more effective in NK competent in comparison with NK deficient mice (FIG. 8C).

Figure Legends

FIG. 1 Expression of ED-B FN in human pancreatic carcinoma and in two orthotopic nude mouse models of pancreatic cancer. ED-B FN expression was quantified by computer aided image analysis. Values given represent the immunostained area as a percentage of measurement frame area with the lines indicating the mean ED-B FN amount of each group. *: p<0.001 versus human pancreatic carcinoma.

FIG. 2 Therapeutic effects of L19IL2 against orthotopic pancreatic cancer in nude mice. A-C Nude mice were orthotopically injected with the human pancreatic cancer cell line DanG. After establishment of solid tumors, groups of 10-12 mice were randomly treated as indicated for 10 days (days 7-11, 14-18 after tumor cell transplantation). All mice were sacrificed on day 21 and tumor volume was calculated (A, C). (A) Left panel: Mice were administered with either 0.9% saline or with the indicated concentrations of IL-2 equivalents as either L19IL2 or untargeted IL-2. Data shown represent the mean tumor volume±SEM of each treatment group. *: p<0.004 (versus control); +: p=0.0003 (versus equimolar amounts of IL-2). Right panel: Mice were treated with saline, 4.29 MIU/kg BW L19IL2 or equimolar amounts of the homodimeric scFvL19 antibody fragment. Values are expressed as the percentage of tumor volume from vehicle treated controls. *: p≦0.004 (versus control and L1 g). (B) Left panel: Blood samples were collected from mice bearing tumors ranging between 8 and 908 mm$^3$ in volume and from tumor-free mice which served as negative controls. Serum concentrations of CA 19-9 were determined by chemiluminescence immunoassay and CA 19-9 level versus tumor volume was plotted for each individual animal. N=56, r=0.7332, p<0.0001. Right panel: Blood samples from mice treated with vehicle or L19IL2 were collected at the indicated time points and serum CA 19-9 levels were determined. Each point represents the mean±SEM of control or treatment group. *: p<0.05. (C) Mice were randomly assigned to the indicated treatment groups. At the end of treatment, blood samples were collected and serum lipase was analyzed by a kinetic calorimetric assay. Values shown are the mean±SEM of each treatment group. (D) Nude mice were orthotopically transplanted with the human pancreatic cancer cell line MiaPaca. Solid tumor were allowed to become established until day 40 and mice were subsequently treated with saline or the indicated concentrations of either L19IL2 or untargeted IL-2 on days 40-44, 47-51 after tumor cell inoculation. All mice were killed at day 54 and the tumor volume was calculated. Data shown are expressed as the mean±SEM of each treatment group. *: p≦0.0007 (versus control); +, p=0.0003 (L19IL2 1.43 MIU/kg BW versus equimolar amounts of IL-2); ‡: p=0.0513 (L19IL2 4.29 MIU/kg BW versus equimolar amounts of IL-2).

Figure 3:
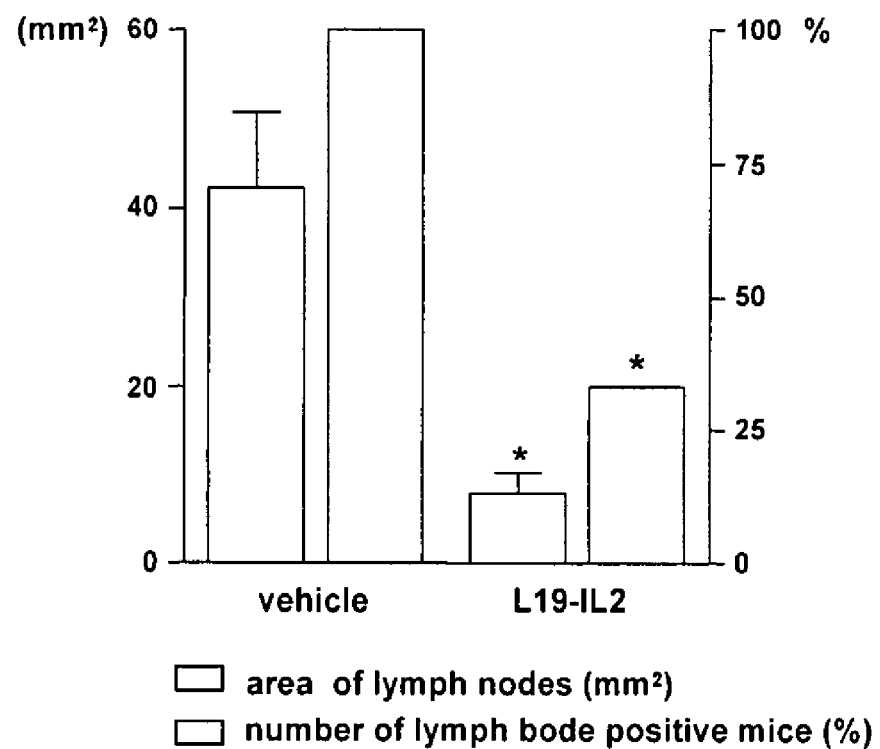

FIG. 3 Therapeutic effects of L19IL2 on established metastases of orthotopic pancreatic cancer xenografts in nude mice. Nude mice were orthotopically injected with cells of the human pancreatic cancer cell line MiaPaca, stably transfected with an Angiopoetin-2 DNA construct, resulting in metastatic spread of pancreatic cancer to intraabdominal lymph nodes and liver. The area of lymph nodes was calculated by determining the largest diameter and its perpendicular diameter and computing the product of the two measurements. Values given represent the median lymph node area±SEM of control and treatment group. Lymph nodes were analyzed for tumor infiltration by immunostaining for pancytokeratin. The results of human specific DNA PCR are summarized in the figure. Data given represent the number of mice having PCR positive lymph nodes as the percentage of vehicle- or L19IL2 treated mice, respectively *: p=0.0275.

FIG. 4 Schedule dependent anti-tumor effects of L19-IL-2. Nude mice bearing orthotopic DanG pancreatic tumors were i.v. administered with vehicle (0.9% saline) or 4.29 MIU/kg BW L19IL2 according to the treatment schedules depicted on the left panel. All mice were killed at day 21 and pancreatic tumor volume was calculated (right panel). Data shown represent the mean±SEM of each treatment group. *: p≦0.0001 versus saline control.

FIG. 5 Long term effects of L19IL2 treatment. 10 nude mice bearing orthotopic DanG pancreatic cancer were treated with 4.29 MIU/kg BW L19IL2 on days 7-11, 14-18 after tumor cell transplantation and were subsequently left untreated. At the end of therapy and repeated biweekly, mouse blood samples were collected and serum CA 19-9 levels were determined. Data shown represent the serum CA 19-9 levels of each individual animal.

FIG. 6 Efficacy of treatment with L19-IL-2, gemcitabine and a combination thereof on pancreatic cancer in nude mice. Mice, bearing orthotopic DanG pancreatic tumors were subjected to i.p. treatment with 250 mg/kg BW gemcitabine once weekly (days 7, 14), i.v. injection of 4.29 MIU/kg BW L19IL2 on days 8-12, 15-19, combinatorial treatment of L19IL2 and gemcitabine or vehicle (0.9% saline) treatment. At day 21, all mice were euthanized and tumor volume was calculated. Results are expressed as the mean±SEM of each treatment group. * P<0.01 versus control, x: p<0.01 versus gemcitabine, +: p=0.0435 versus L19-IL-2.

FIG. 7 Effects of L19IL2 on tumor necrosis, apoptosis and proliferation. Mice bearing orthotopic DanG tumors were i.v. treated with either 0.9% saline or 4.29 MIU/kg BW L19IL2. Left panel: After termination of therapy, tumors were examined by conventional H&E staining (A), apoptosis was assessed by TUNEL assay (B) and proliferating cells were visualized by Ki67 staining (C). Representative examples of vehicle-treated and L19IL2 treated tumors are shown. Right panel: (A) For quantification of necrosis, necrotic and total tumor area was marked at low power (×2.5). The areas were calculated by computer aided image analysis system and the ratio tumor necrosis area/total tumor area is given in percentages. Data shown represent the mean±SEM of each group * P=0.0159. For quantification of apoptosis (B)—and proliferation index (C), the ratio of positive tumor cells/all tumor cells was computed. Results are expressed in percentages and represent the mean±SEM of each group. *: P=0.0177. (A, scale bar 500 μm, B,C, scale bar 100 μm).

FIG. 8 Identification of the immune effector cells mediating L19IL2 induced tumor regression. (A, B) Nude mice, bearing orthotopic DanG pancreatic tumors were i.v. administered with 0.9% saline or 4.29 MIU/kg BW L19-IL-2. After completion of therapy, tumors were stained with a CD 11b antibody recognizing predominantly macrophages (A) and with an NK1.1 antibody specific for NK cells (B). Left panel: Representative examples of vehicle-treated (and L19IL2 treated mice are shown. (Bar, 100 μm). Infiltration of CD 11b+ cells (A) and of NK cells (B) was quantified via computer aided image analysis. Results given represent the immunostained area as a percentage of measurement frame area and are expressed as the mean±SEM of each group. * P=0.0159 (A), * P=0.0012 (B). (C) Nude mice, bearing orthotopic DanG tumors were randomly assigned to the indicated treatment groups. After cessation of therapy, tumor volume was determined. Bars represent the mean±SEM of each group. * P<0.01 versus any other group.

We claim:

1. A combination comprising at least (i) a fusion protein and (ii) gemcitabine, wherein the fusion protein comprises
an antibody part comprising a V heavy chain comprising the sequence set forth in SEQ ID NO: 1 and a V light chain comprising the sequence set forth in SEQ ID NO: 2 and which binds to the $ED_b$-fibronectin domain and
an Interleukin-2 part.

2. A combination according to claim 1,
wherein the fusion protein has an N-terminal antibody part and a C-terminal Interleukin-2 part or
wherein the fusion protein has an N-terminal Interleukin-2 part and a C-terminal antibody-part.

3. A combination according to claim 1, wherein the fusion protein has a fusion protein linker connecting the antibody part and the Interleukin-2 part.

4. A combination according to claim 1, wherein the antibody part specifically binds to the $ED_b$ oncofetal fibronectin domain with sub-nanomolar affinity.

5. A combination according to claim 1, wherein the antibody part comprises one V heavy chain according to SEQ ID NO: 1 and one V light chain according to SEQ ID NO: 2.

6. A combination according to claim 1, wherein the heavy and the light chain are connected by an antibody linker.

7. A combination according to claim 6, wherein the antibody linker comprises a sequence comprising at least 90% identity to the sequence set forth in SEQ ID NO: 3.

8. A combination according to claim 1, wherein the Interleukin-2 part is human Interleukin-2 or a functional variant thereof.

9. A combination according to claim 1, wherein the Interleukin-2 part comprises a sequence according to SEQ ID NO: 4.

10. A combination according to claim 1, wherein a fusion protein linker connects the antibody-part and the Interleukin-2 part.

11. A combination according to claim 10, wherein the fusion protein linker has a length of 1 to 30 amino acids.

12. A combination according to claim 10, wherein the fusion protein linker comprises a sequence according to SEQ ID NO: 5.

13. A combination according to claim 1, wherein gemcitabine is gemcitabine hydrochloride.

14. A medicament which comprises the combination according to claim 1 and a solvent.

15. A pharmaceutical composition comprising the combination according to claim 1 and a pharmaceutically acceptable carrier or diluent.

16. A kit comprising, in separate packages, the fusion protein and the gemcitabine according to claim 1.

17. A method for treating cancer in a subject in need thereof, comprising administering to the subject a therapeutically effective amount of the combination according to claim 1.

18. A method according to claim 17, wherein the cancer is non-small cell lung cancer, head and neck cancer, ovarian cancer or breast cancer.

19. A method according to claim 17, wherein the cancer is pancreatic cancer.

20. A combination according to claim 6, wherein the antibody linker comprises the sequence set forth in SEQ ID NO: 3.

* * * * *

SEQUENCE LISTING

<160> NUMBER OF SEQ ID NOS: 11

<210> SEQ ID NO 1
<211> LENGTH: 116
<212> TYPE: PRT
<213> ORGANISM: Artificial
<220> FEATURE:
<221> NAME/KEY: DOMAIN
<222> LOCATION: (1)..(116)
<223> OTHER INFORMATION: Antibody-VH-Region from L19

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 2
<211> LENGTH: 108
<212> TYPE: PRT
<213> ORGANISM: Artificial
<220> FEATURE:
<221> NAME/KEY: DOMAIN
<222> LOCATION: (1)..(108)
<223> OTHER INFORMATION: Antibody-VL-Region from L19

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 3
<211> LENGTH: 12
<212> TYPE: PRT
<213> ORGANISM: Artificial
<220> FEATURE:

```
<221> NAME/KEY: DOMAIN
<222> LOCATION: (1)..(12)
<223> OTHER INFORMATION: Antibody linker region

<400> SEQUENCE: 3

Gly Asp Gly Ser Ser Gly Gly Ser Gly Gly Ala Ser
1               5                   10

<210> SEQ ID NO 4
<211> LENGTH: 133
<212> TYPE: PRT
<213> ORGANISM: Homo sapiens
<220> FEATURE:
<221> NAME/KEY: DOMAIN
<222> LOCATION: (1)..(133)
<223> OTHER INFORMATION: human Interleukin-2

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 5
<211> LENGTH: 17
<212> TYPE: PRT
<213> ORGANISM: Artificial
<220> FEATURE:
<221> NAME/KEY: DOMAIN
<222> LOCATION: (1)..(17)
<223> OTHER INFORMATION: Fusion Protein linker

<400> SEQUENCE: 5

Glu Phe Ser Ser Ser Gly Ser Ser Ser Gly Ser Ser Ser
1               5                   10                  15

Gly

<210> SEQ ID NO 6
<211> LENGTH: 5
<212> TYPE: PRT
<213> ORGANISM: Artificial
<220> FEATURE:
<221> NAME/KEY: DOMAIN
<222> LOCATION: (1)..(5)
<223> OTHER INFORMATION: CDR1 VH L19

<400> SEQUENCE: 6

Ser Phe Ser Met Ser
1               5
```

<210> SEQ ID NO 7
<211> LENGTH: 7
<212> TYPE: PRT
<213> ORGANISM: Artificial
<220> FEATURE:
<221> NAME/KEY: DOMAIN
<222> LOCATION: (1)..(7)
<223> OTHER INFORMATION: CDR3 VH L19

<400> SEQUENCE: 7

Pro Phe Pro Tyr Phe Asp Tyr
1               5

<210> SEQ ID NO 8
<211> LENGTH: 17
<212> TYPE: PRT
<213> ORGANISM: Artificial
<220> FEATURE:
<221> NAME/KEY: DOMAIN
<222> LOCATION: (1)..(17)
<223> OTHER INFORMATION: CDR2 VH L19

<400> SEQUENCE: 8

Ser Ile Ser Gly Ser Ser Gly Thr Thr Tyr Tyr Ala Asp Ser Val Lys
1               5                   10                  15

Gly

<210> SEQ ID NO 9
<211> LENGTH: 12
<212> TYPE: PRT
<213> ORGANISM: Artificial
<220> FEATURE:
<221> NAME/KEY: DOMAIN
<222> LOCATION: (1)..(12)
<223> OTHER INFORMATION: CDR1 Vl L19

<400> SEQUENCE: 9

Arg Ala Ser Gln Ser Val Ser Ser Ser Phe Leu Ala
1               5                   10

<210> SEQ ID NO 10
<211> LENGTH: 7
<212> TYPE: PRT
<213> ORGANISM: Artificial
<220> FEATURE:
<221> NAME/KEY: DOMAIN
<222> LOCATION: (1)..(7)
<223> OTHER INFORMATION: CDR2 Vl L19

<400> SEQUENCE: 10

Tyr Ala Ser Ser Arg Ala Thr
1               5

<210> SEQ ID NO 11
<211> LENGTH: 9
<212> TYPE: PRT
<213> ORGANISM: Artificial
<220> FEATURE:
<221> NAME/KEY: DOMAIN
<222> LOCATION: (1)..(9)
<223> OTHER INFORMATION: CDR3 Vl L19

<400> SEQUENCE: 11

Gln Gln Thr Gly Arg Ile Pro Pro Thr
1               5